United States Patent
Peterson et al.

(10) Patent No.: US 11,642,009 B2
(45) Date of Patent: May 9, 2023

(54) MOBILE PHONE-MOUNTED PERISCOPE AND HEALTHCARE SYSTEMS AND METHODS USING A MOBILE PHONE-MOUNTED PERISCOPE FOR RECORDING PERSONAL HEALTH STATUS FOR REMOTE AND AUTOMATED DIAGNOSES

(71) Applicant: DentiScope Inc., Santa Cruz, CA (US)

(72) Inventors: Anders Peterson, Madrid (ES); Victor Sánchez Alonso, Madrid (ES)

(73) Assignee: DentiScope Inc., Santa Cruz, CA (US)

( * ) Notice: Subject to any disclaimer, the term of this patent is extended or adjusted under 35 U.S.C. 154(b) by 187 days.

(21) Appl. No.: 17/246,556

(22) Filed: Apr. 30, 2021

(65) Prior Publication Data
US 2021/0377374 A1    Dec. 2, 2021

Related U.S. Application Data

(60) Provisional application No. 63/018,373, filed on Apr. 30, 2020.

(51) Int. Cl.
*A61B 1/00* (2006.01)
*G06N 20/00* (2019.01)
(Continued)

(52) U.S. Cl.
CPC ...... *A61B 1/00105* (2013.01); *A61B 1/00163* (2013.01); *G02B 23/08* (2013.01);
(Continued)

(58) Field of Classification Search
CPC ......... G06T 7/0012; G06T 2207/30036; G06T 7/0016; G06T 7/11; G06T 17/20; G06T 2210/41; G06T 2207/10048; G06T 2207/10116; G06T 5/009; G06T 7/0014; G06T 2200/32; G06T 2207/10024;
(Continued)

(56) References Cited

U.S. PATENT DOCUMENTS

| | | |
|---|---|---|
| 4,727,416 A | 2/1988 | Cooper et al. |
| 5,051,823 A | 9/1991 | Cooper et al. |

(Continued)

OTHER PUBLICATIONS

Anantharaman, Rajaram, et al., "Oro Vision: Deep Learning for Classifying Orofacial Diseases", 2017 IEEE International Conference on Healthcare Informatics, DOI: 10.1109/ICHI.2017.69, (Year: 2017), pp. 39-45.

(Continued)

*Primary Examiner* — Golam Sorowar
(74) *Attorney, Agent, or Firm* — Sheppard, Mullin, Richter & Hampton LLP

(57) ABSTRACT

Dental periscopes having mounting clips configured to couple to mobile devices are disclosed. A patient can mount the dental periscope to a mobile device by coupling the mounting clip of the periscope to the mobile device. The patient can then use the mobile device-mounted dental periscope to capture image and/or video data of one or more dental structures. The captured image/video data can be sent to a remote system to obtain a remote dental diagnosis based on the captured data. The remote diagnosis may be an automated diagnosis generated by a trained machine learning classifier.

13 Claims, 23 Drawing Sheets

(51) Int. Cl.
*G02B 23/08* (2006.01)
*G06T 7/00* (2017.01)
*H04M 1/02* (2006.01)
*H04M 1/04* (2006.01)

(52) U.S. Cl.
CPC ........... *G06N 20/00* (2019.01); *G06T 7/0012* (2013.01); *H04M 1/0264* (2013.01); *H04M 1/04* (2013.01); *G06T 2207/20081* (2013.01); *G06T 2207/30036* (2013.01)

(58) Field of Classification Search
CPC . G06T 2207/20208; G06T 2207/20212; G06T 2210/22; G06T 3/40; G06T 3/4038; G06T 3/60; G16H 30/40; G16H 30/20; G16H 40/67; G16H 10/60; G16H 40/63; G16H 50/20; G16H 20/40; G16H 40/20; G16H 15/00; G16H 80/00; G16H 50/70; G16H 10/40; G16H 70/00; G16H 50/30; G16H 50/50; G16H 70/20; G16H 40/40; G16H 50/80; G16H 70/60; G16H 20/00; A61B 1/24; A61B 5/0088; A61B 5/0022; A61B 5/445; A61B 1/0684; A61B 2576/02; A61B 5/1176; A61B 5/0077; A61B 1/000095; A61B 1/00016; A61B 1/0607; A61B 5/6898; A61B 1/00045; A61B 1/00105; A61B 1/247; A61B 1/00032; A61B 1/0004; A61B 1/00087; A61B 1/045; A61C 13/0004; A61C 13/34; A61C 19/004; A61C 3/00; A61C 9/0073; A61C 7/002; A61C 9/0053; A61C 7/08; A61C 7/146; A61C 19/04; A61C 1/084; A61C 1/088; A61C 5/90; A61C 17/00; A61C 19/043; H04N 5/2256; H04N 5/2354; H04N 5/2253; H04N 2005/2255; H04N 5/232; H04N 5/2252; H04N 5/2254; H04N 5/2257; H04N 5/23238; H04N 5/23241; H04N 7/183; H04N 5/23222; H04N 13/239; H04N 13/296
See application file for complete search history.

(56) References Cited

U.S. PATENT DOCUMENTS

| | | | |
|---|---|---|---|
| 8,210,757 | B2 | 7/2012 | Sterns et al. |
| 2016/0051142 | A1 | 2/2016 | Howes |
| 2018/0284580 | A1* | 10/2018 | Matthews ................ A61B 1/05 |
| 2022/0000342 | A1* | 1/2022 | Knecht ................... G03B 17/14 |
| 2022/0338723 | A1* | 10/2022 | Farkash ................. A61B 1/053 |

OTHER PUBLICATIONS

Anantharaman, Rajaram, et al., "Utilizing Mask R-CNN for Detection and Segmentation of Oral Diseases", 2018 IEEE International Conference on Bioinformatics and Biomedicine (BIBM), (Year: 2018), pp. 2197-2204.

Liang, Yuan, et al., "OralCam: Enabling Self-Examination and Awareness of Oral Health Using a Smartphone Camera", CHI'16, May 7-12, 2016, arXiv:2001.05621v2, 13 pages.

Song, Bofan, et al., "Automatic Classification of Dual-Modalilty, Smartphone-Based Oral Dysplasia nad Malignancy Images Using Deep Learning", Biomedical Optics Express, vol. 9, No. 11, Nov. 1, 2018, pp. 5318-5329.

You, Wenzhe, et al., "Deep Learning-Based Dental Plaque Detection on Primary Teeth: A Comparison with Clinical Assessments", BMC Oral Health, vol. 20, No. 141, 2020, https://doi.org/10.1186/s12903-020-01114-6, 7 pages.

Zhang, Xuan, et al., "Development and Evaluation of Deep Learning for Screening Dental Caries from Oral Photographs", Oral Diseases, Wiley Periodicals LLC, Nov. 17, 2020, DOI: 10.1111/odi.13735, 9 pages.

* cited by examiner

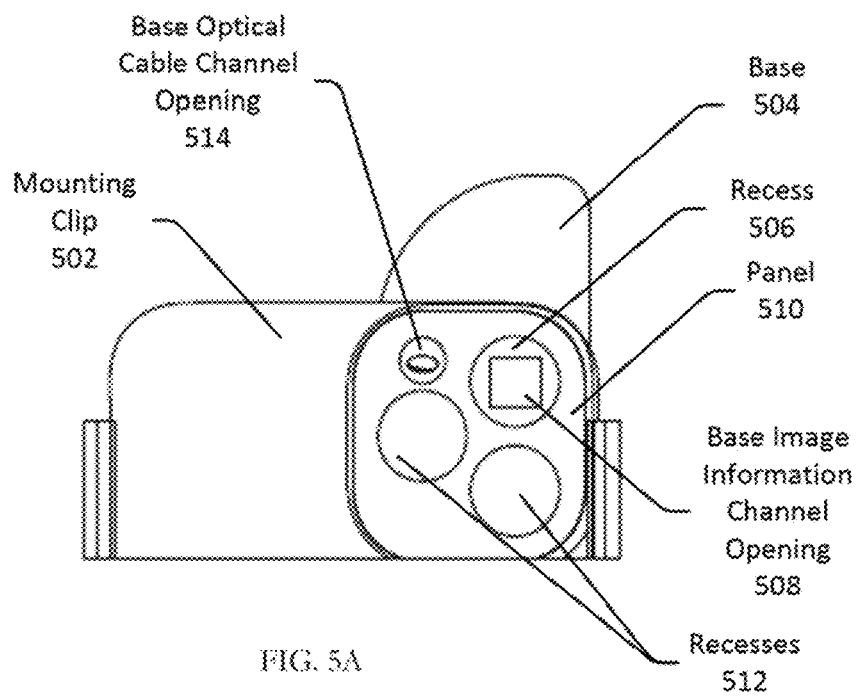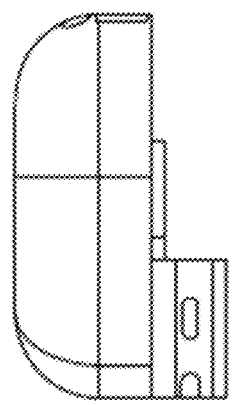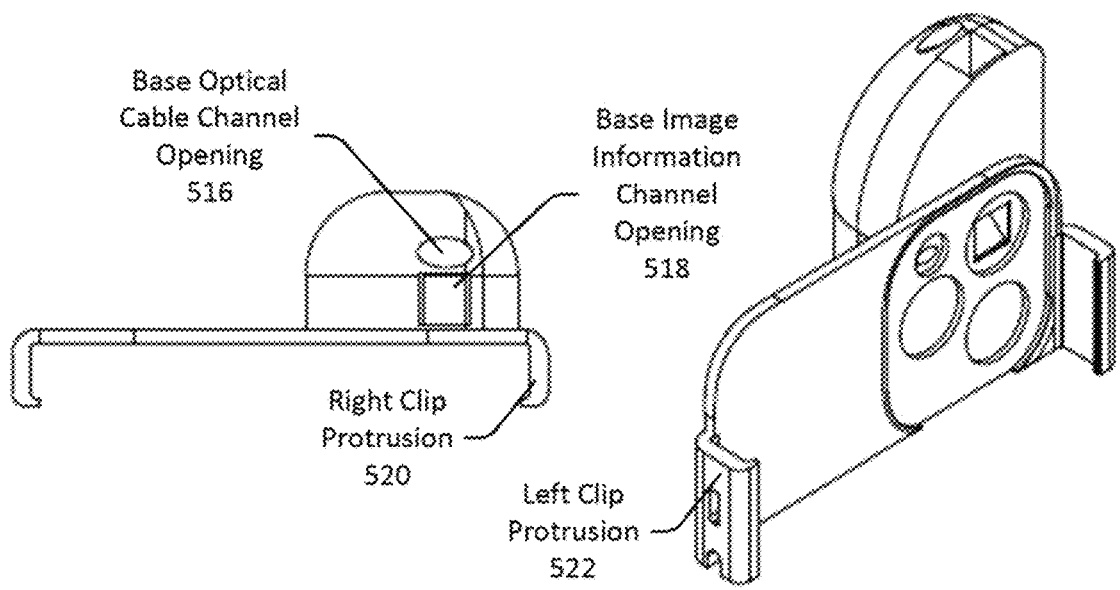
FIG. 5A
FIG. 5B
FIG. 5C
FIG. 5D

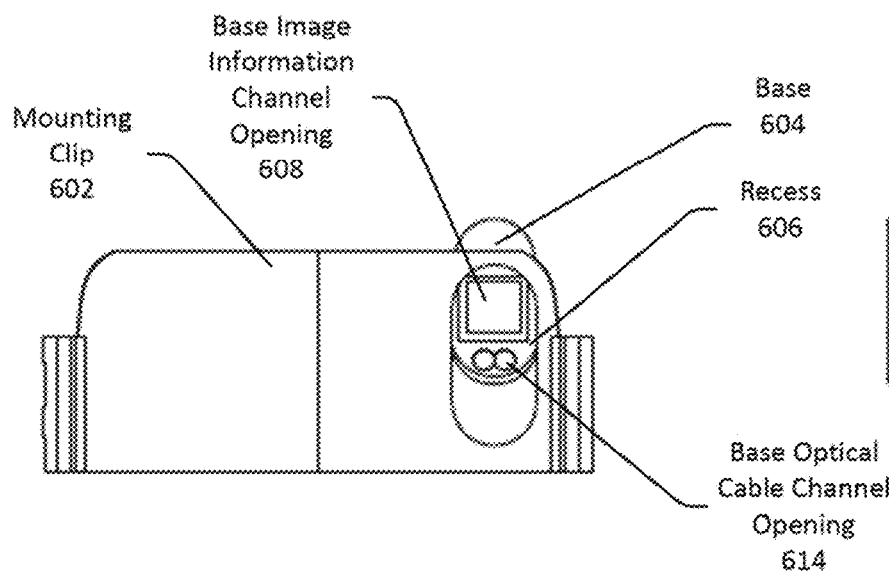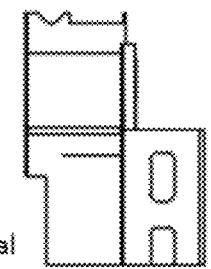
FIG. 6A  FIG. 6B
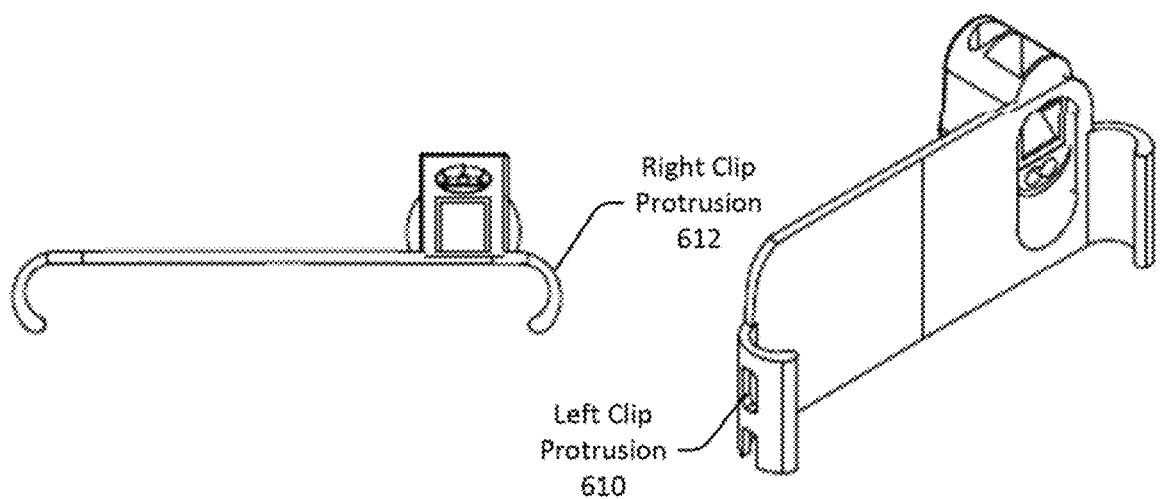
FIG. 6C  FIG. 6D

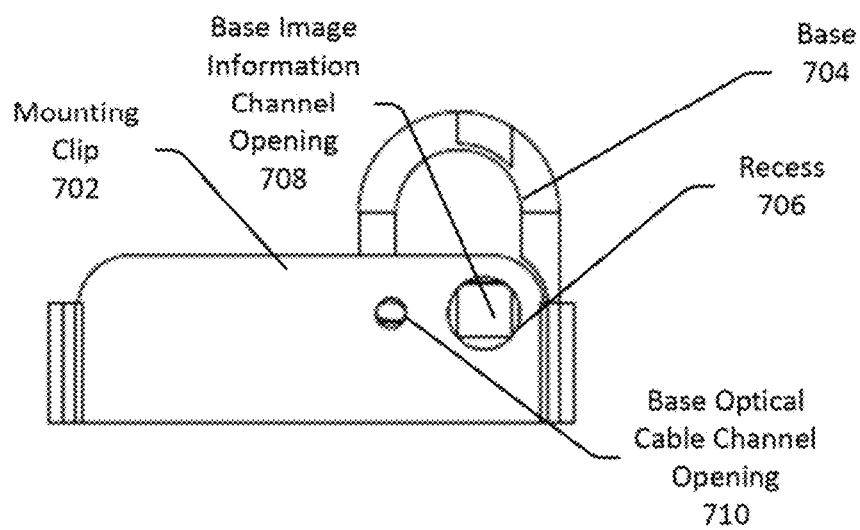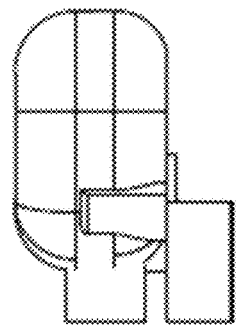
FIG. 7A          FIG. 7B
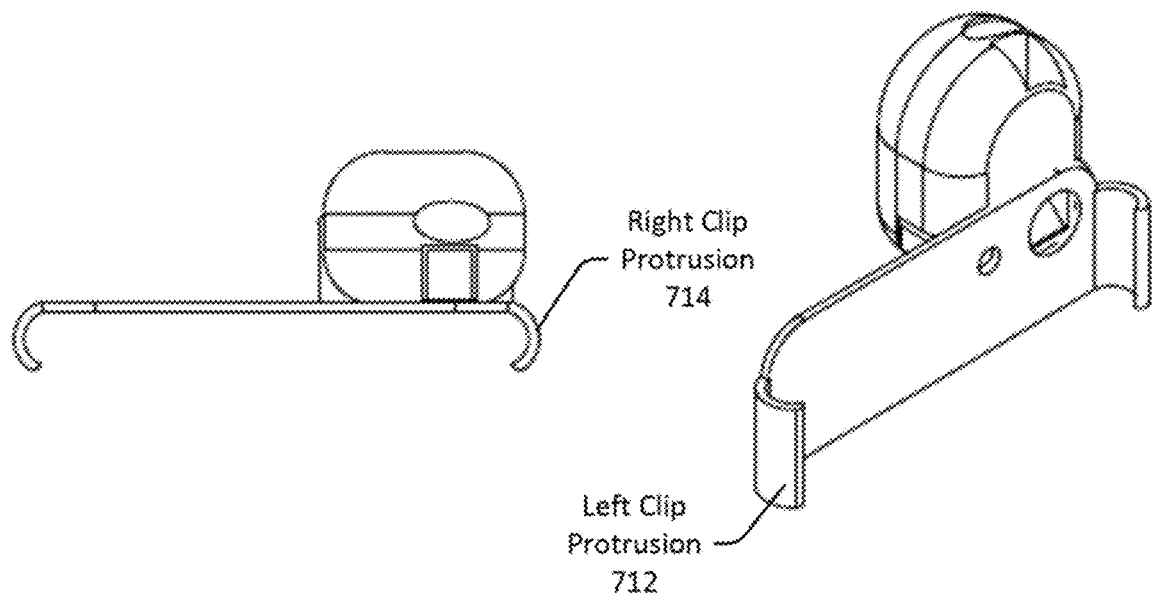
FIG. 7C          FIG. 7D

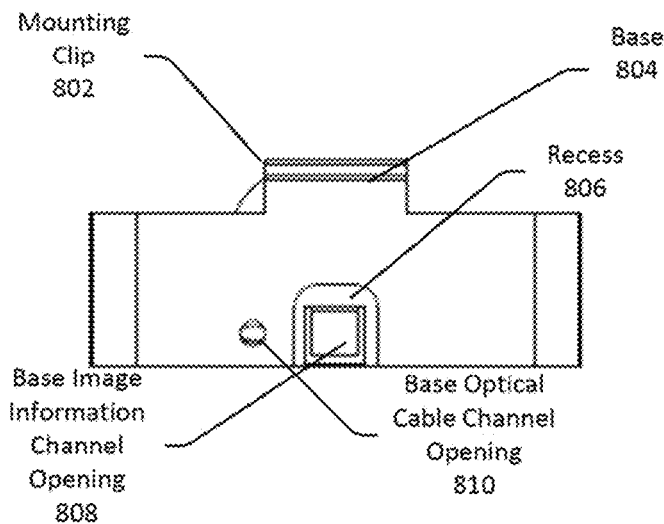
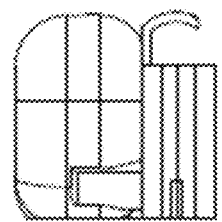
FIG. 8A　　　　　　　　　　　FIG. 8B
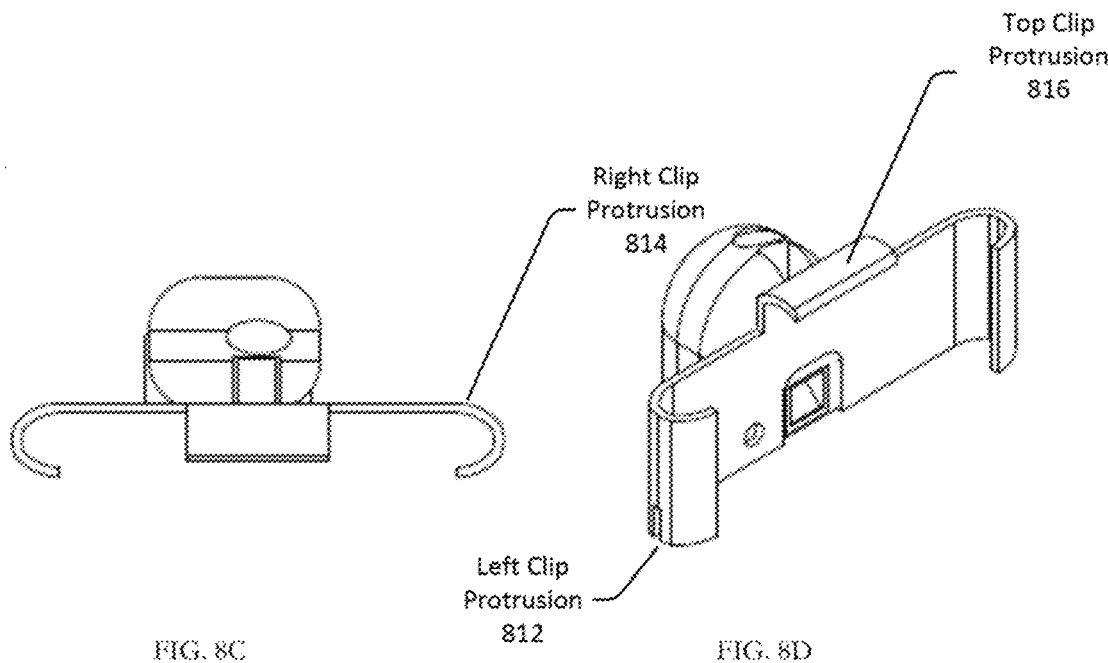
FIG. 8C　　　　　　　　　　　FIG. 8D

MOBILE PHONE-MOUNTED PERISCOPE AND HEALTHCARE SYSTEMS AND METHODS USING A MOBILE PHONE-MOUNTED PERISCOPE FOR RECORDING PERSONAL HEALTH STATUS FOR REMOTE AND AUTOMATED DIAGNOSES

CROSS-REFERENCE TO RELATED APPLICATION(S)

This application claims the benefit of U.S. Provisional Application No. 63/018,373, filed on Apr. 30, 2020, the content of which is incorporated in its entirety herein.

TECHNICAL FIELD

This disclosure pertains to dental periscopes, and more particularly to dental periscopes with mounting clips configured to couple to mobile devices. This disclosure also pertains to machine learning systems and algorithms for generating remote automated diagnoses of dental conditions based on image/video data captured using the dental periscopes.

BACKGROUND

Telemedicine and other remote health services have gained popularity in recent years. Improved video calling functionality, enhanced network connectivity, and the ubiquity of mobile devices has fueled the adoption of telemedicine as a potentially viable alternative to in-person healthcare visits. Further, there are a number of scenarios in which patients may prefer a remote visit with a doctor or dentist to an in-person visit such as if the patient is traveling, cannot take off work, lives in a remote area, does not want to risk infection in a public setting or otherwise prefers to avoid public settings, cannot afford in-person visits, or the like. A number of technical challenges still exist for remote health services, especially remote dental visits.

SUMMARY

Example embodiments of the present invention relate to dental periscopes with mounting clips configured to couple to mobile devices. A patient can mount the dental periscope to a mobile device by coupling the mounting clip of the periscope to the mobile device. The patient can then use the mobile device-mounted dental periscope to capture image and/or video data of one or more dental structures. The captured image/video data can be sent to a remote device to obtain a remote diagnosis of one or more dental conditions based on the image/video data. Diagnostic information indicative of the remote diagnosis can then be sent to the mobile device for presentation to the patient. The remote diagnosis may be an automated diagnosis provided by a trained machine learning model.

In an embodiment, a mobile device-mountable periscope for dental imaging is disclosed. The mobile device-mountable periscope includes a head having a head image information channel opening configured to receive image information and a base having a base image information channel opening configured to provide the image information to an image sensor of a mobile device. The periscope further includes an elongated member connecting the head and the base, a head prism disposed within the head, and a base prism disposed within the base. The head prism is configured to redirect the image information that enters the head image information channel opening into the elongated member and towards the base and the base prism is configured to redirect the image information from the elongated member towards the base image information channel opening and towards the image sensor of the mobile device.

In an embodiment, the head prism is a right-angled prism having a first surface that faces the head opening, a second surface perpendicular to the first surface along respective first edges of the first and second surfaces, the second surface facing the elongated member, and a third diagonal surface that connects respective second edges of the first and second surfaces.

In an embodiment, the base prism is a right-angled prism having a first surface that faces the base opening, a second surface perpendicular to the first surface along respective first edges of the first and second surfaces, the second surface facing the elongated member, and a third diagonal surface that connects respective second edges of the first and second surfaces.

In an embodiment, the mobile device-mountable periscope further includes a head image information channel disposed within the head, an elongated member image information channel disposed with the elongated member, and a base image information channel disposed within the base.

In an embodiment, the head prism is configured to redirect the image information from the head image information channel into the elongated member image information channel and towards the base image information channel, In an embodiment, the base prism is configured to redirect the image information from the elongated member image information channel into the base image information channel and towards the base opening.

In an embodiment, the base of the mobile device-mountable is coupled to a mounting clip configured to mount the periscope on a mobile device.

In an embodiment, the base image information channel opening faces at least one camera of the mobile device when the mounting clip is attached to the mobile device.

In an embodiment, the mobile device-mountable periscope further includes one or more optical cables disposed within the elongated member, where the one or more optical cables are adapted to carry light from a light source of the mobile device to the head image information channel opening.

In an embodiment, the head of the mobile device-mountable periscope includes a head optical cable channel, the base includes a base optical cable channel, and the elongated member includes an elongated member optical cable channel, such that the one or more optical cables are contained within head optical cable channel, the base optical cable channel, and the elongated optical cable channel.

In an embodiment, the base of the mobile device-mountable periscope includes one or more base optical channel openings for receiving the one or more optical cables.

In an embodiment, the mounting clip includes a light blocking element disposed between the base image information channel opening and the one or more base optical channel openings.

In an embodiment, the mounting clip includes a recess and the base image information channel opening is formed in the recess.

In an embodiment, the head image information channel includes a pair of prism supports that support the head prism within the head image information channel.

In an embodiment, the mounting clip is integrally formed with the base.

In an embodiment, the base is detachably coupled to the elongated member.

In another embodiment, a mounting clip for mounting a dental periscope to a mobile device is disclosed. The mounting clip includes a first opening that faces at least one camera of a mobile device when the mounting clip is attached to the mobile device and at least one second opening that faces a light source of the mobile device when the mounting clip is attached to the mobile device, where the mounting clip is configured to mount a dental periscope to the mobile device.

In an embodiment, the mounting clip is integrally formed with the dental periscope.

In an embodiment, the mounting clip is detachably coupled to the dental periscope.

In an embodiment, the mounting clip includes a light blocking element disposed between the first opening and the at least one second opening.

In another embodiment, a computer-vision-based method for identifying a dental condition based on image data captured by a mobile device is disclosed. The method includes receiving image data from a client application executing on a mobile device, the image data being captured via a dental periscope mounted on the mobile device, the image data including at least one dental image; providing the image data as input to a machine learning model configured to generate automated diagnoses of dental conditions; obtaining an output from the machine learning model, the output identifying one or more dental conditions associated with the at least one dental image; and sending diagnosis information indicative of the output from the machine learning model to the mobile device for presentation via a user interface of the client application.

In an embodiment, the method further includes training the machine learning model using ground-truth patient image data that is labeled to indicate confirmed dental conditions associated with the ground-truth patient image data.

These and other features of the devices, systems, and methods disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention.

BRIEF DESCRIPTION OF THE DRAWINGS

Certain features of various embodiments of the present technology are set forth with particularity in the appended claims. A better understanding of the features and advantages of the technology will be obtained by reference to the following detailed description that sets forth illustrative embodiments, in which the principles of the invention are utilized, and the accompanying drawings of which:

FIG. 5A is a front view of a mounting clip coupled to a base of a dental periscope, where the mounting clip is configured to couple to a first phone model in accordance with some embodiments of the invention.

FIG. 5B is a side view of the mounting clip and periscope base of FIG. 5A.

FIG. 5C is a top view of the mounting clip and periscope base of FIG. 5A.

FIG. 5D is a perspective view of the mounting clip and periscope base of FIG. 5A.

FIG. 6A is a front view of a mounting clip coupled to a base of a dental periscope, where the mounting clip is configured to couple to a second phone model in accordance with some embodiments of the invention.

FIG. 6B is a side view of the mounting clip and periscope base of FIG. 6A.

FIG. 6C is a top view of the mounting clip and periscope base of FIG. 6A.

FIG. 6D is a perspective view of the mounting clip and periscope base of FIG. 6A.

FIG. 7A is a front view of a mounting clip coupled to a base of a dental periscope, where the mounting clip is configured to couple to a third phone model in accordance with some embodiments of the invention.

FIG. 7B is a side view of the mounting clip and periscope base of FIG. 7A.

FIG. 7C is a top view of the mounting clip and periscope base of FIG. 7A.

FIG. 7D is a perspective view of the mounting clip and periscope base of FIG. 7A.

FIG. 8A is a front view of a mounting clip coupled to a base of a dental periscope, where the mounting clip is configured to couple to a fourth phone model in accordance with some embodiments of the invention.

FIG. 8B is a side view of the mounting clip and periscope base of FIG. 7A.

FIG. 8C is a top view of the mounting clip and periscope base of FIG. 7A.

FIG. 8D is a perspective view of the mounting clip and periscope base of FIG. 7A.

DETAILED DESCRIPTION

Figure 1:
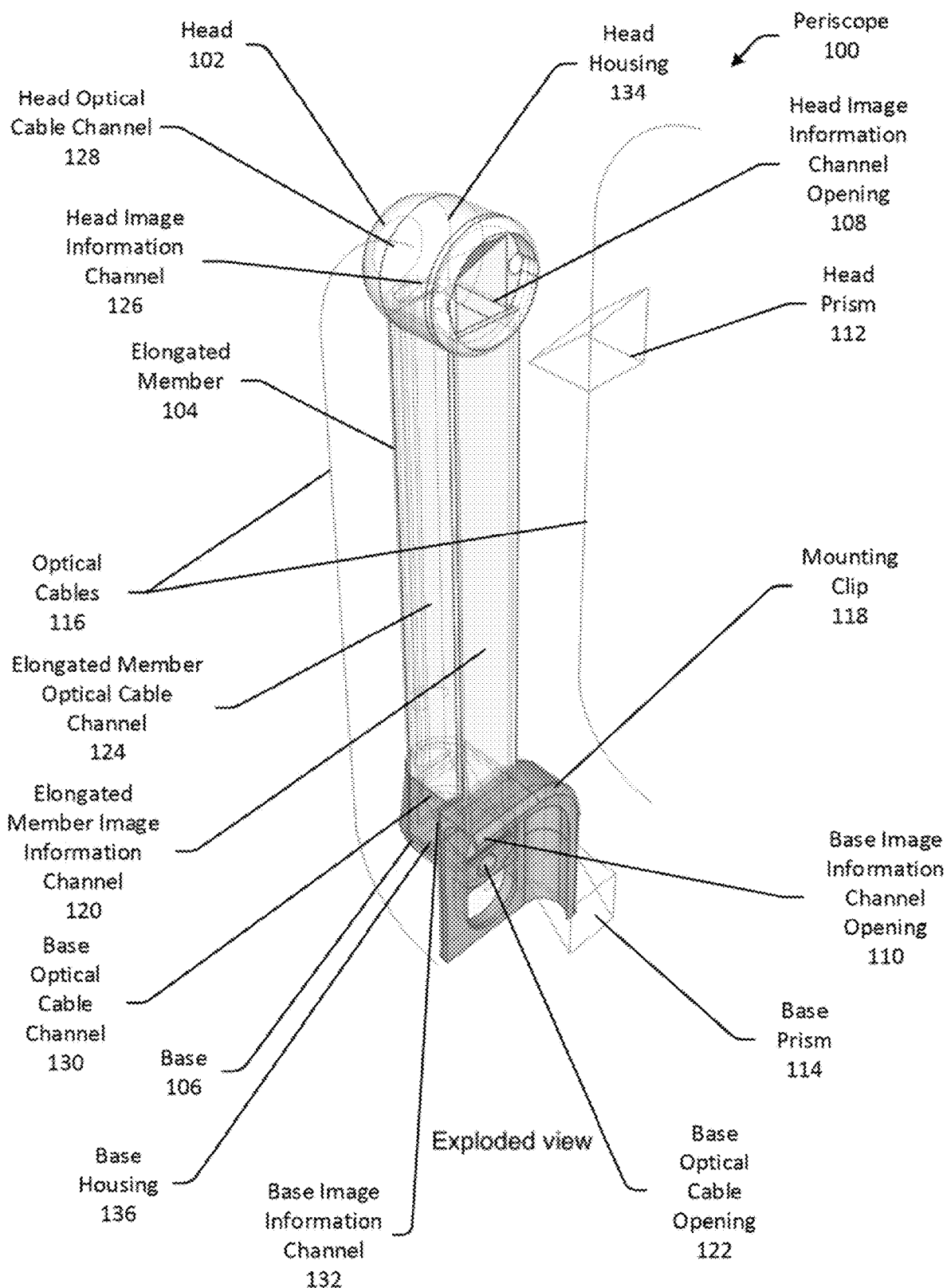
FIG. 1 is an exploded perspective view of a dental periscope with mounting clip in accordance with some embodiments of the invention.

Example embodiments of the present invention relate to dental periscopes with mounting clips configured to couple to mobile devices. In some embodiments, a periscope and mounting clip disclosed herein may be a single, integrally formed unit. A patient can mount the dental periscope to a mobile device by coupling the mounting clip of the periscope to the mobile device. The patient can then use the mobile device-mounted dental periscope to capture image and/or video data of one or more dental structures. The dental structures can include one or more surfaces of teeth, gums, cheeks, the tongue, the roof of the mouth, the base of the mouth, lips, or any other internal oral structure.

In some embodiments, the patient may be guided in real-time via instructions provided through a patient application running on the mobile device to capture images/video of specific dental structures or images/video from specific angles. In other embodiments, real-time instructions may not be provided, and the patient may capture the image/video data independently. In some embodiments, the patient application may send the captured patient image/video data to a remote dentist system. A dentist may access the captured data using a dentist application executing on the remote dentist system and review the data to provide a diagnosis of one or more dental conditions. Diagnosis information indicative of the one or more diagnosed dental conditions may then be sent to the patient application and presented to the patient via a user interface of the patient application.

In some embodiments, previously captured patient image/video data may be annotated/labeled to indicate confirmed diagnosed dental conditions associated with the image/video data. This labeled dataset can be provided as ground-truth training data to an artificial intelligence (AI)/machine learning (ML) model (also referred to herein as an AI/ML engine). Once trained, the AI/ML model can be used to provide computer-vision-based automated remote diagnoses of dental conditions based on image/video data of a patient's dental structures. In some embodiments, the output of the trained AI/ML model can be confirmed or rejected by a dentist or other trained professional, and this human judgment can be used to provide feedback to the model such that the model's classification capabilities can be refined.

While example embodiments of the present invention may be described herein with respect to periscopes used specifically to facilitate the capture of images and/or video of dental structures, it should be appreciated that the periscopes disclosed herein can be used to facilitate the capture of images and/or video of any part of a body, and the captured data can be evaluated to diagnose any suitable medical condition. More generally, embodiments of the present invention are applicable to any setting in which remote healthcare services are being delivered. In addition, data captured via a mobile device-mounted periscope will be described hereinafter as image data or simply as images for ease of explanation, but should be understood as including video data and/or image data.

FIG. 1 is an exploded perspective view of a dental periscope 100 in accordance with some embodiments of the invention. In some embodiments, upon mounting the periscope 100 to a mobile device, e.g., via a mounting clip 118 of the periscope 100, the mobile-device-mounted periscope 100 can be used to facilitate the capture of images of dental structures of a patient by an image sensor (e.g., camera) of the mobile device. The periscope 100 includes a head 102 and a base 106 connected by an elongated member 104. The mounting clip 118 may be integrally formed with the base 106. In fact, in some embodiments, the periscope 100 may include the head 102, the base 106, the elongated member 104, and the mounting clip 118 as a single integrally formed unit. In other embodiments, one or more of these components may be removably coupled. For instance, the mounting clip 118 may be removably coupled to the base 106 and/or the elongated member may be removably coupled to the base 106 and/or the head 102.

The head 102 includes a head housing 134 having a head image information channel 126 therein. The head image information channel 126 may have a substantially rectangular (e.g., square) cross-section through a length of the head housing 134; however, other cross-sectional shapes (e.g., circular, oval, rectangular, polygonal, etc.) are contemplated. A head prism 112 may be provided within the head image information channel 126. The head image information channel 126 includes a head image information channel opening 108. In some embodiments, the head image information channel opening 108 is substantially rectangular; however, other shapes are contemplated as well. In some embodiments, the head prism 112 may be positioned within the head image information channel 126 such that a face of the prism 112 substantially encompasses an entirety of the head image information channel opening 108.

The base 106 includes a base housing 136 having a base image information channel 132 formed therein. The base image information channel 132 may have a substantially rectangular cross-section through a length of the base housing 136; however, other cross-sectional shapes (e.g., circular, oval, rectangular, polygonal, etc.) are similarly also contemplated. A base prism 114 may be provided within the base image information channel 132. In some embodiments, the base image information channel opening 110 is substantially rectangular; however, other shapes are contemplated as well. In some embodiments, the base prism 114 may be positioned within the base image information channel 132 such that a face of the prism 114 substantially encompasses an entirety of the base image information channel opening 110.

The elongated member 104 may include a single, continuously formed body or may be formed of multiple sections coupled together via one or more coupling mechanisms. The length of the elongated member 104 may be sufficient to enable the head 102 to reach the backside of the wisdom teeth of an adult, e.g., 3" or longer. In some embodiments, the elongated member 104 includes an elongated member housing with multiple channels therein including an elongated member image information channel 120 and an elongated member optical cable channel 124. The elongated member image information channel 120 may have a substantially rectangular cross-section taken across a width of the periscope 100; however, other cross-sectional shapes (e.g., circular, oval, rectangular, polygonal, etc.) are contemplated. The elongated member optical cable channel 124 may have a substantially oval cross-section taken across a width of the periscope 100; however, other cross-sectional shapes, including any of those previously mentioned are contemplated as well. Optical cables 116 that transmit light from a light source of the mobile device may extend within the elongated member optical cable channel 124. The optical cables 116 may be received from a base optical cable channel 130 and may be provided to a head optical cable channel 128.

As will be described in more detail below, image information that enters the head image information channel 126 via the head image information opening 108 may be redirected by the head prism 112 towards the elongated member image information channel 120. The image information may travel through the elongated member image information channel 120 and may be redirected again by the base prism 114 in the base image information channel 132 towards the base image information channel opening 110 in the base 106 and ultimately to the phone's image sensor.

In example scenarios, the mobile device-mounted periscope 100 may be physically manipulated by a patient so that the head 102 faces (or potentially physically contacts) a dental structure of which the patient wants to capture an image. The head image information opening 108 is configured to receive image information of the dental structure that the patient wants to image. The image information may be generated based on light reflecting off of surface(s) of the dental structure. The head prism 112 may be configured to redirect the incoming image information that enters the head image information channel 126 through the head image information opening 108 to the elongated member image information channel 120. In some embodiments, the head prism 112 may be a right-angled prism having a first surface that faces the head opening 108, a second surface perpendicular to the first surface along respective first edges of the first and second surfaces such that the second surface faces the elongated member 104, and a third diagonal surface that connects respective second edges of the first and second surfaces. In some embodiments, the image information may pass through one of the perpendicular surfaces of the head prism 112 and be redirected (reflected and/or refracted) by the diagonal surface towards the other perpendicular surface. The image information may pass through this other perpendicular surface and into the elongated member image information channel 120.

The image information redirected by the head prism 112 from the head image information channel 126 into the elongated member image information channel 120 may be redirected again by the base prism 114 disposed in the base image information channel 132. In some embodiments, similar to the head prism 112, the base prism 114 may be a right-angled prism having perpendicular first and second surfaces that meet at respective first edges, where the first and second surfaces face the base channel opening 110 and the elongated member 104, respectively, and a third diagonal surface connecting respective second edges of the first and second surfaces. In some embodiments, incoming image information from the elongated member image information channel 120 may pass through one of the perpendicular surfaces of the base prism 114 and be redirected (reflected and/or refracted) by the diagonal surface towards the other perpendicular surface of the base prism 114. The image information may pass through this other perpendicular surface and travel towards the base image information channel opening 110. Thus, the base image information channel 132 of the base 106 may receive the image information from the elongated member image information channel 120, and the base prism 114 disposed in the base image information channel 132 may be configured to redirect the image information towards the base channel opening 110, and ultimately towards an image sensor of the mobile device. In some embodiments, the head prism 112 and/or the base prism 114 may be configured to redirect the image information through a combination of refraction and internal reflection. While the example periscope 100 depicted in FIG. 1 includes prisms for redirecting the image information, it should be appreciated that any suitable optical element configured to provide a similar reflection and/or refraction mechanism can be used.

In some embodiments, the base 106 of the periscope 100, and optionally a lower portion of the elongated member 104 may be formed of relatively opaque materials to mitigate the effects of light escaping from the periscope 100, of light transferring between channels, or of light from an external environment interfering with proper operation of an image sensor of the mobile device, which would diminish the quality of the captured images. In some embodiments, the base 106, and optionally other portions of the periscope 100 in relative proximity to the image sensor of the mobile device may be formed of multiple different materials with different relative opacities to form a gradation of opacities such that the more opaque materials are located more proximally to the image sensor.

The optical cables 116 disposed within the elongated member optical cable channel 124 of the elongated member 104 may be any suitable light transmission media such as rigid optical fiber, flexible optical fiber, or the like. The optical cables 116 may be configured to carry light emitted by a light source of the mobile device to the head image information channel opening 110 to illuminate dental structures to be imaged. The light source may be, for example, one or more light emitting diodes. The base 106 may include a base optical cable opening 122 configured to receive the optical cables 116 such that the optical cables 116 face a light source of the mobile device when the periscope 100 is mounted to the mobile device.

Figure 2A:
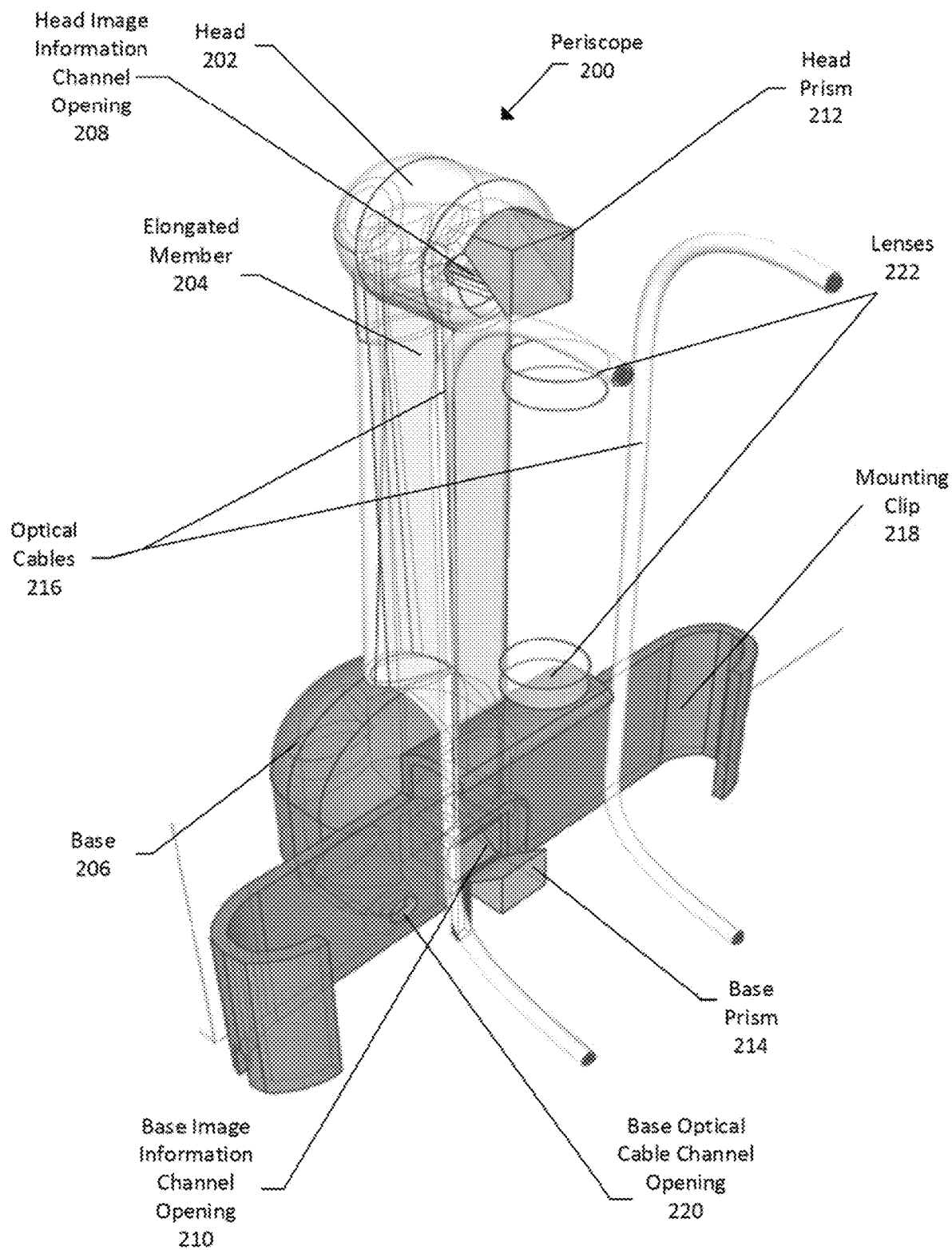
FIG. 2A is another exploded perspective view of a dental periscope with mounting clip in accordance with some embodiments of the invention.

FIG. 2A is an exploded perspective view of a dental periscope 200 in accordance with some embodiments of the invention. It should be appreciated that while certain components of the dental periscope 200 may not be identified with a reference numeral in FIG. 2A, any such component may have a similar function and may be similarly located within the periscope 200 as a correspondingly named component in FIG. 1.

Similar to the periscope 100, the periscope 200 includes a head 202 including a head housing, a head image information channel within the head housing, and a head image information channel opening 208 at a distal end of the head image information channel that is configured to receive the image information. The head 202 is coupled to a base 206 via an elongated member 204. The base 206 includes a base housing, a base image information channel, and a base image information channel opening 210 at a distal end of the base image information channel configured to provide the image information to the image sensor of the mobile device. The periscope 200 further includes a head prism 212 positioned within the head image information channel and a base prism 214 positioned within the base image information channel, each prism being configured to provide similar functions to the first and base prisms 112, 114 of the periscope 100. In addition, the periscope 200 includes optical cables 216 that carry light from the light source of the mobile device to the head image information channel opening 208 for illuminating an object to be imaged. While not explicitly denoted in FIG. 2, in some embodiments, the elongated member 204 includes an elongated member optical cable channel configured to contain the optical cables 216 and further includes an elongated member image transmission channel configured to transmit the image information, similar to periscope 100.

In the embodiment of FIG. 2A, the periscope 200 further includes one or more lenses 222. The lenses 222 may be disposed within the elongated member 204. More specifically, the lenses 222 may be disposed within the elongated member image information channel of the elongated member 204. In some embodiments, the lenses 222 may be disposed at different vertical positions within the elongated member image information channel. The lenses 222 may include refractive properties that enhance a field-of-view (FOV) of the image information that is received at the head image information channel opening 208, and which is redirected by the head prism 212 through the head image information channel into the elongated member image information channel and towards the base image information channel of the base 206, and which is again redirected by the base prism 214 through a base image information channel towards the base image information channel opening 210, and ultimately towards the image sensor of the mobile device.

In some embodiments, a focal length of the lenses 222 and/or prisms with particular indices of refraction may be selected to ensure a threshold clarity/quality of the image information regardless of where the head 202 is positioned in a patient's mouth. For example, the lenses 222 may be selected to have focal lengths that are based on a length, width, and/or depth of the head housing so that image clarity is maintained even if a distal end of the head 202 physically contacts the oral structure being imaged. Further, in some embodiments, dimensions may be chosen for the depth and/or forward projection length of the head 202 to ensure that a clear image is captured even if a distal end of the head 202 physically contacts an oral structure. The lenses 222 may have a substantially circular lateral cross-section through a center of the lenses 222. Outer surfaces of the lenses 222 may be convex and/or concave.

The periscope 200 further includes a mounting clip 218 configured to couple the base 206 of the periscope 200 to a mobile device. In some embodiments, the mounting clip 218 is integrally formed with the base 206. In such embodiments, the periscope 200 may be considered to include at least the head 202, the elongated member 204, the base 206, and the mounting clip 218. In some embodiments, the integrally formed mounting clip 218 and base 206 may be removably coupled to the elongated member 204. In such embodiments, the base 206 and mounting clip 218 may form an integral component that can be swapped out with other base and mounting clip combinations designed for different models having different arrangements of the image sensor(s) and light source. That is, in some embodiments, the base 206 and mounting clip 218 may be designed to have a specific arrangement of openings that align with corresponding components of a mobile device (e.g., a light source, an image sensor, etc.) when the periscope 200 is mounted to the mobile device using the mounting clip 218.

In some embodiments, the mounting clip 218 may be removably coupled to the base 206. In such embodiments, the periscope 200 may be considered to include at least the head 202, the elongated member 204, and the base 206, while the mounting clip 218 may be treated as a distinct component from the periscope 200. In some embodiments, the base 206 may be formed with multiple different arrangements of openings that match multiple corresponding arrangements of image sensor(s) and light source(s) of different mobile phone models. In such embodiments, different mounting clips with different configurations of openings that match the different phone models can be interchangeably coupled to the single base 206, such that for any given arrangement of openings in the mounting clip 218, the base 206 includes a corresponding arrangement of openings that align with the openings in the mounting clip 218 when the mounting clip 218 is coupled to the base 206.

In other embodiments, the base 206 may be removably coupled to the elongated member 204 and the mounting clip 218 may be removably coupled to the base 206. In such embodiments, multiple bases 206 may be provided, each with one or more arrangements of openings designed to accommodate one or more corresponding mounting clips 218. In this manner, a "mix-and-match" capability may be provided by which different combinations of bases 206 and mounting clips 218 may be used. In addition, the periscope 200 and mounting clip 218 may be more compactly stored in those embodiments in which the base 206 and the mounting clip 218 are removably coupled to one another and to the elongated member 204.

Figure 2B:
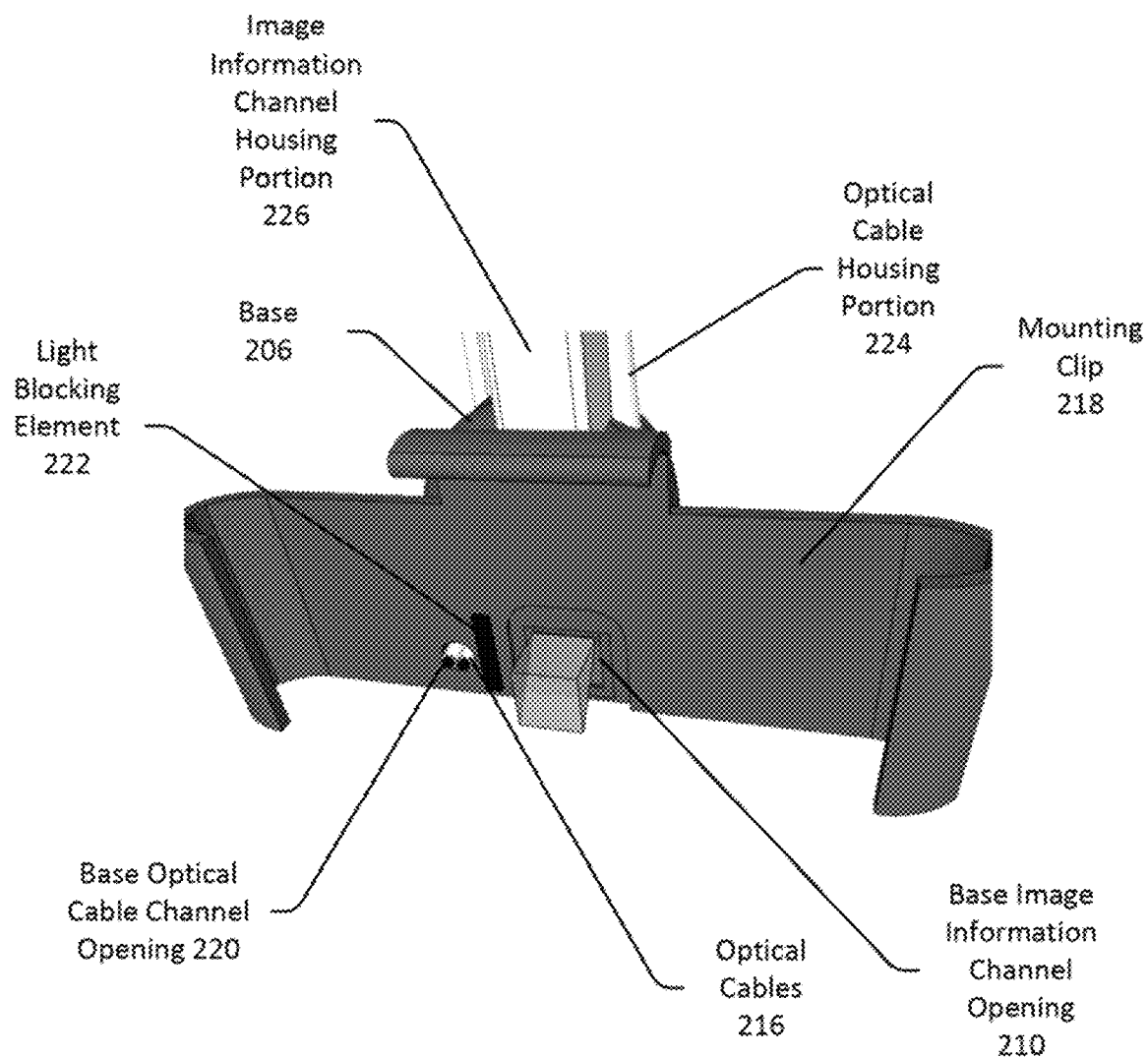
FIG. 2B is a more detailed perspective view of a mounting clip and other components of a dental periscope in accordance with some embodiments of the invention.

In some embodiments, the various components of the periscope 200 may be formed of any of a variety of types of materials including, without limitation, plastics, metals, cemented carbides, ceramics, etc. In some embodiments, different components of the periscope 200 may be formed of different materials. For instance, the elongated member 204 may be formed of a plastic material while the head 202 may be formed of a cemented carbide material, diamond composite material, or the like in order to provide the head 202 with enhanced durability against wear. Similarly, the mounting clip 218 may be formed of a lightweight metal such as aluminum, a plastic material, or the like. The mounting clip 218 and/or components of the periscope 200 may be manufactured using any of a variety of manufacturing techniques including, without limitation, injection molding, additive manufacturing (e.g., 3D printing), high-speed machining, and the like FIG. 2B is a more detailed perspective view of a mounting clip 218 and other components of the dental periscope 200 in accordance with some embodiments of the invention. As shown in FIG. 2B, the mounting clip 218 includes the base optical cable channel opening 220 that is configured to receive the optical cables 216. While a single optical cable opening 220 is depicted as receiving multiple optical cables 216, in some embodiments each optical cable 216 may be received by a respective base optical cable channel opening. Further, as shown in FIG. 2B, a light blocking element 222 may be affixed to the mounting clip 218. In some embodiments, the light blocking element 222 is affixed between the base optical cable channel opening 220 that receives the optical cables 216 and the base image information channel opening 210. In some embodiments, the mounting clip 218 is removably coupled to the base 206. In those embodiments, the mounting clip 218 may include respective openings that align with the base optical cable channel opening 220 and the base image information channel opening 210, respectively, when the mounting clip 218 and the base 206 are coupled together.

The light blocking element 222 may function as a physical barrier between the light source of the mobile device and the image sensor of the mobile device to prevent or otherwise mitigate light emitted by the light source from entering the image information channel of the elongated member 204 of the periscope 200 (e.g., via the base image information channel and base image information channel opening 210). If light from the light source enters an image information channel of the periscope 200, the light could interfere with the image sensor's ability to capture a clear image of the image information. The light blocking element 222 may be a plastic foam material having a high opacity or any other suitable material having light blocking attributes.

Also shown in FIG. 2B is an optical cable housing portion 224 and an image information channel housing portion 226. The optical cable housing portion 224 and the image information channel housing portion may together constitute an elongated member housing of the elongated member 204. The elongated member optical cable channel may be contained within the optical cable housing portion 224 and the elongated member image information channel may be contained within the image information channel housing portion 226. In some embodiments, the housing portion 224 may be located behind the housing portion 226.

Figure 3A:
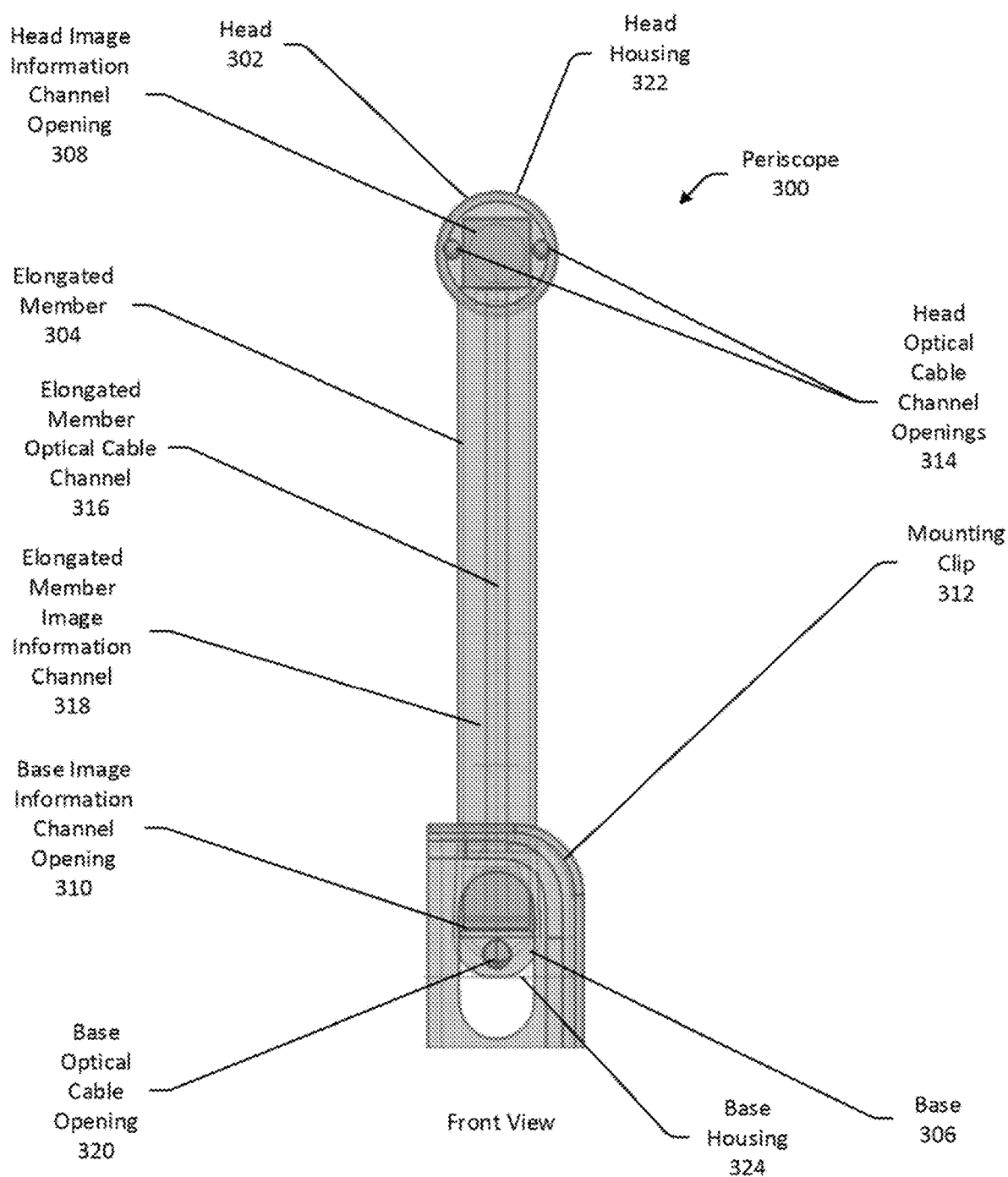
FIG. 3A is a front view of a dental periscope in accordance with some embodiments of the invention.
Figure 3B:
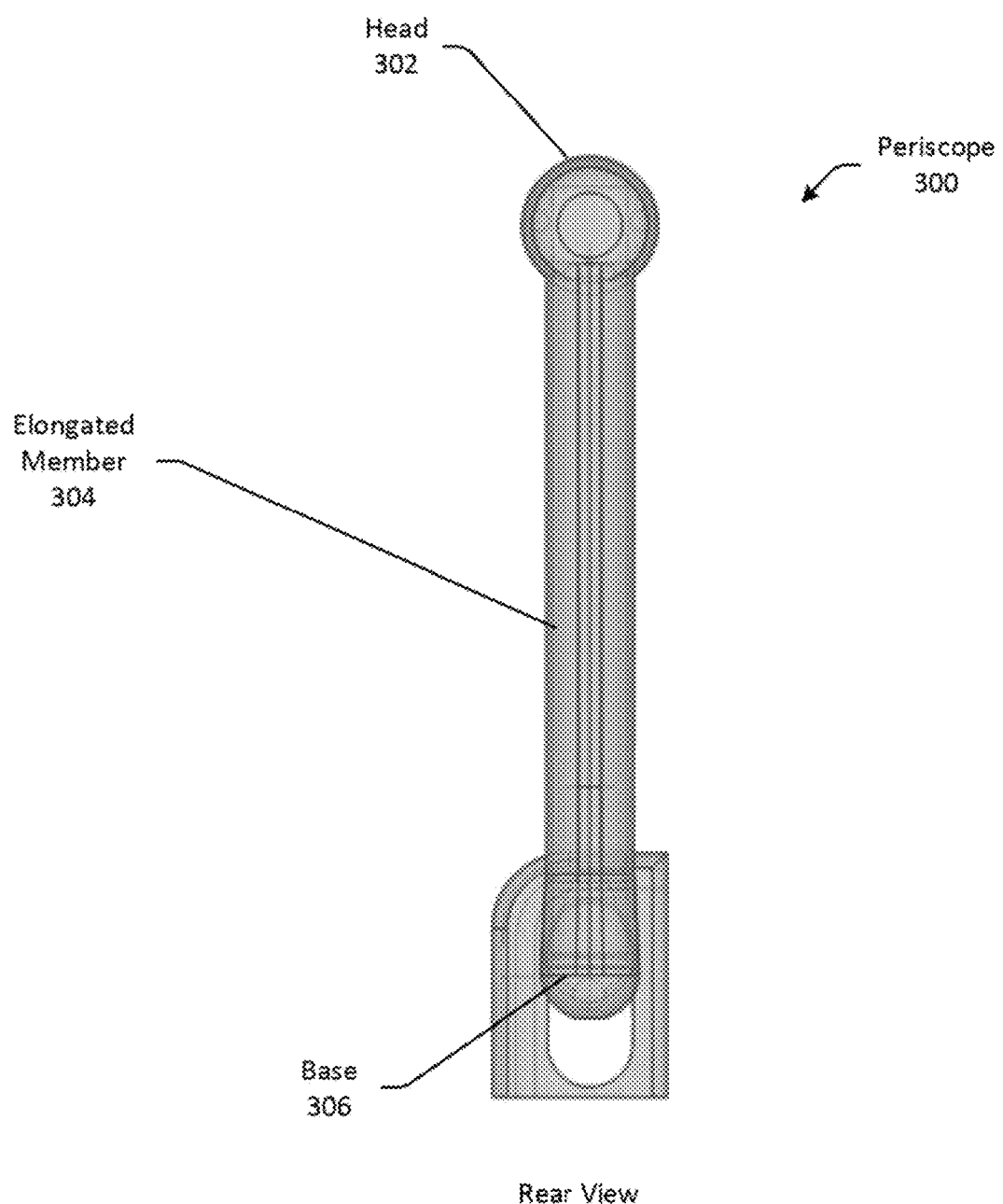
FIG. 3B is a rear view of a dental periscope of FIG. 3A.
Figure 3C:
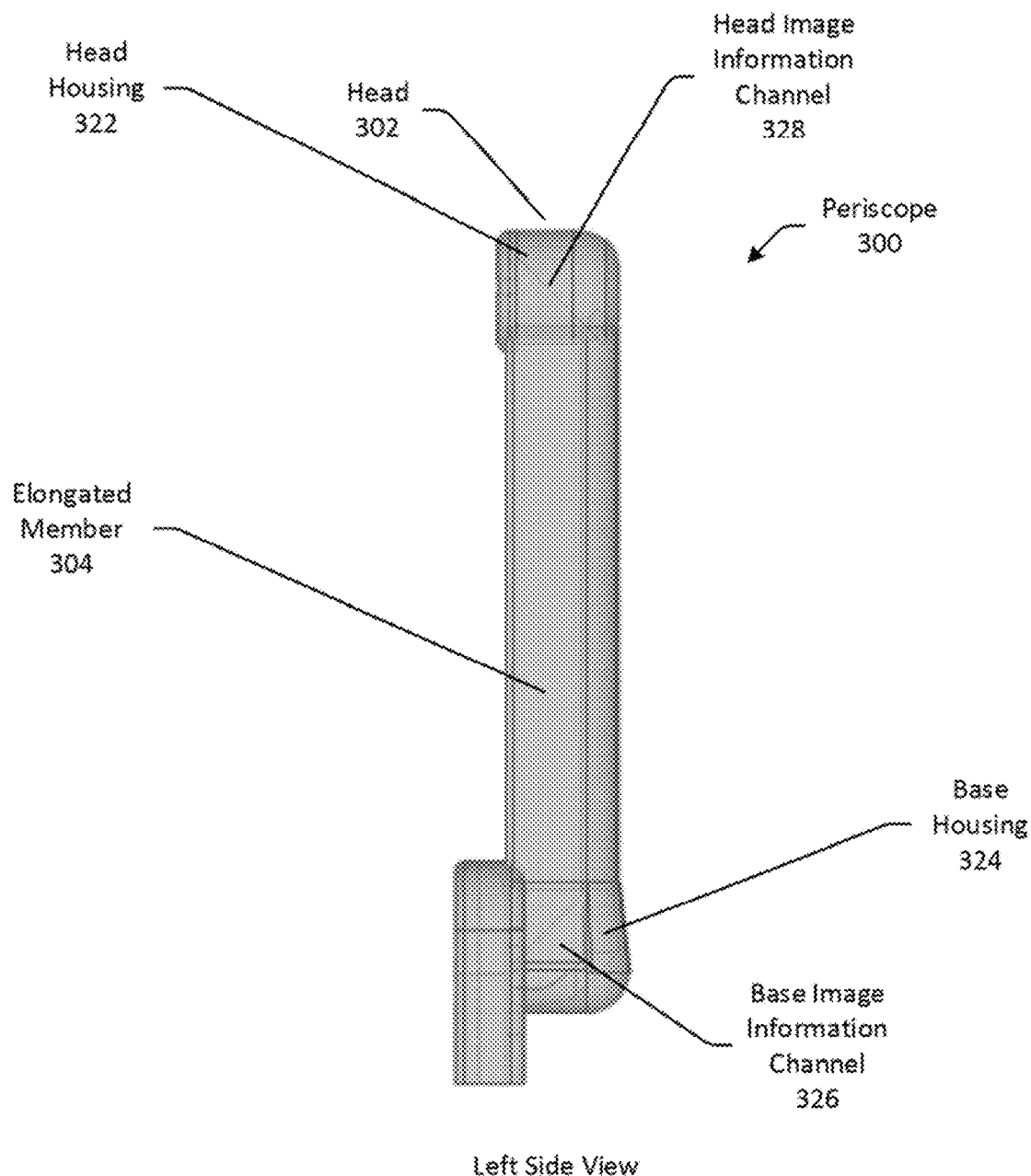
FIG. 3C is left side view of the dental periscope of FIG. 3A.
Figure 3D:
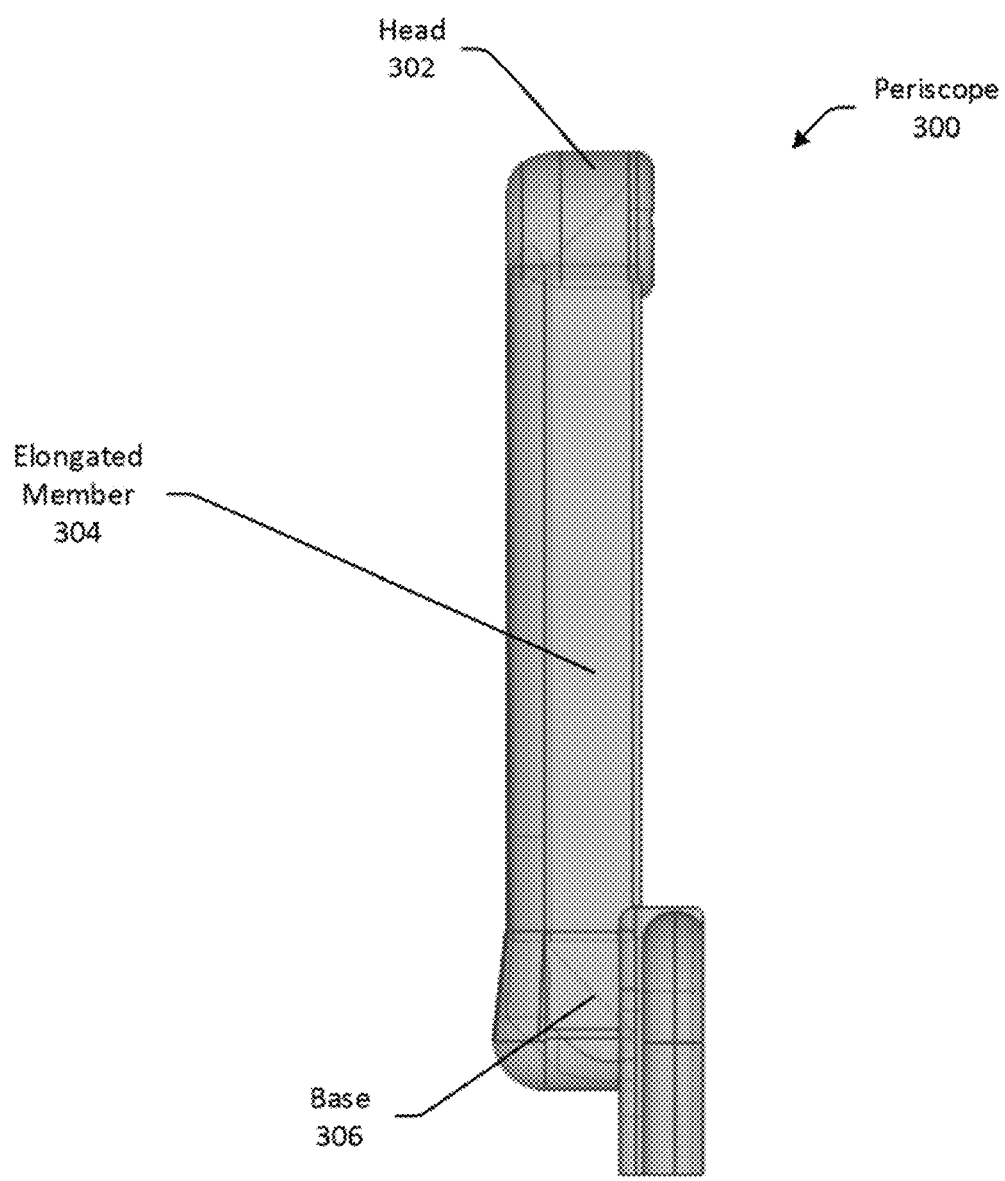
FIG. 3D is a right side view of the dental periscope of FIG. 3A.

FIG. 3A is a front view of a dental periscope 300 in accordance with some embodiments of the invention. FIG. 3B is a rear view of the periscope 300. FIG. 3C is left side view of the periscope 300. FIG. 3D is a right side view of the periscope. The periscope 300 includes components similar to those previously described with respect to periscopes 100 and 200 including a head 302 connected via an elongated member 304 to a base 306. The head 302 includes a head housing 322. A head prism may be disposed within a head image information channel 328 (FIG. 3C) of the head 302 and a base prism may be disposed within a base image information channel 326 (FIG. 3C) of the base 306. The head prism and the base prism may perform substantially the same functions as described earlier in connection with the first and base prisms of periscopes 100 and 200.

In some embodiments, the head 302 may include a substantially rectangular (e.g., square) head image information channel opening 308 having a width and/or a length of about 0.25 inches to about 0.5 inches. The head image information channel 328 within the head 302 may have a cross-section that is also substantially rectangular and substantially the same width as the head image information channel opening 308. In other embodiments, the head image information channel opening 308 may have a different shape (e.g., circular, trapezoidal, etc.) and/or different diameter dimensions and the head image information channel 328 may have a different cross-sectional shape. In some embodiments, a depth of the head image information channel may be about 0.75 inches to about 1 inch.

The head 302 may further include head optical cable channel openings 314 configured to receive the optical cables 316. In some embodiments, the head optical cable channel openings 314 may be slots, grooves, or the like that receive the optical cables 316. In some embodiments, the elongated member optical cable channel 316 may split into two channels within the head 302, and the multiple channels may respectively lead to the head optical cable channel openings 314. In other embodiments, the optical fibers may exit the elongated member optical cable channel when entering the head 302 and be positioned within their respective head optical cable channel openings 314.

The elongated member 304 may be about 2.5 inches to about 3 inches in length. In some embodiments, the elongated member 304 has sufficient length for a distal end of the head 302 to reach any oral structure within a patient's mouth including the back wisdom teeth of an adult or a back portion of the roof of the mouth. In some embodiments, the elongated member 304 may have a length that takes into account a length of a portion of the base 306 that extends above a top of a mobile phone when the periscope 300 is mounted to a mobile phone as well as a length of the head 302/head housing 322. In some embodiments, the elongated member 304 may have a rectangular or substantially square lateral cross-section; however other cross-sectional shapes are contemplated. In some embodiments, the elongated member 304 may contain an elongated member optical cable channel 316 and an elongated member image information channel 318. In some embodiments, and as described in more detail later in this disclosure in relation to FIGS. 5A-5D, the elongated member optical cable channel 316 may have a substantially oval cross-section and the elongated member image information channel 318 may have a substantially rectangular (e.g., square) cross-section. However, other cross-sectional shapes for channels 316, 318 are contemplated.

The base 306 includes a base housing 324 and a base image information channel 326 (FIG. 3C) within the base housing 324. The base 306 may be integrally formed with a mounting clip 312. Alternatively, the mounting clip 312 may be removably coupled to the base 306. The base image information channel opening 310 is at one end of the base image information channel 330 and faces an image sensor of a mobile device when the periscope 300 is coupled to the mobile device. The base image information channel opening 310 may have a substantially rectangular (e.g., square) shape and may have a width and/or a length of about 0.5 inches to about 0.75 inches. The base image information channel 328 may have a longitudinal cross-section taken along a length the channel 328 (corresponding to a vertical direction from the base 306 to the head 302) that is substantially rectangular. The longitudinal cross-section of the base image information channel 328 may have a width and/or a length that is substantially the same as the base image information channel opening 310. In some embodiments, the base channel opening 310 may be sized to have a width and a length that is slightly larger than a diameter of a circular lens of an image sensor (e.g., camera), but not too large so as to overlap with an adjacent cameras lens such as in the case of a phone with a multi-camera configuration.

The base 306 may further include a base optical cable opening 320 configured to receive the optical cables 316. The base optical cable opening 322 may cause the optical cables 316 to face a light source such as an LED of the mobile device 318 when the periscope 300 is coupled to a mobile device. The base optical cable opening 320 may be substantially circular, with a diameter of about 0.2 inches to about 0.3 inches, and thus, may be a smaller opening than the base image information channel opening 310. Dimensions of the base 306 may vary based on the phone model for which the base 306 is designed, and example dimensions of the base 306 and the base image information channel 326 for different mobile device models will be described later in this disclosure.

In some embodiments, the base 306 may include multiple openings such that different combinations of openings align with the light source and camera(s) of different mobile phone models. In some embodiments, multiple base image information channels may be provided within the base 306 and multiple corresponding base image information channel openings formed in the base 306 may match the specific configuration of cameras in mobile phones equipped with multiple cameras. In some embodiments, a prism may be provided within the base 306 at each of the multiple base image information channel openings such that the image information redirected from the head 302 to the base 306 can be captured from any of multiple cameras (e.g., cameras at different zoom levels) within a multi-camera configuration. A patient application—via which captured images may be sent to a dentist application and/or an AI/ML engine for evaluation—may be used to switch, either programmatically or in response to user input, the selection of a particular camera to use to capture the image information.

Figure 3E:
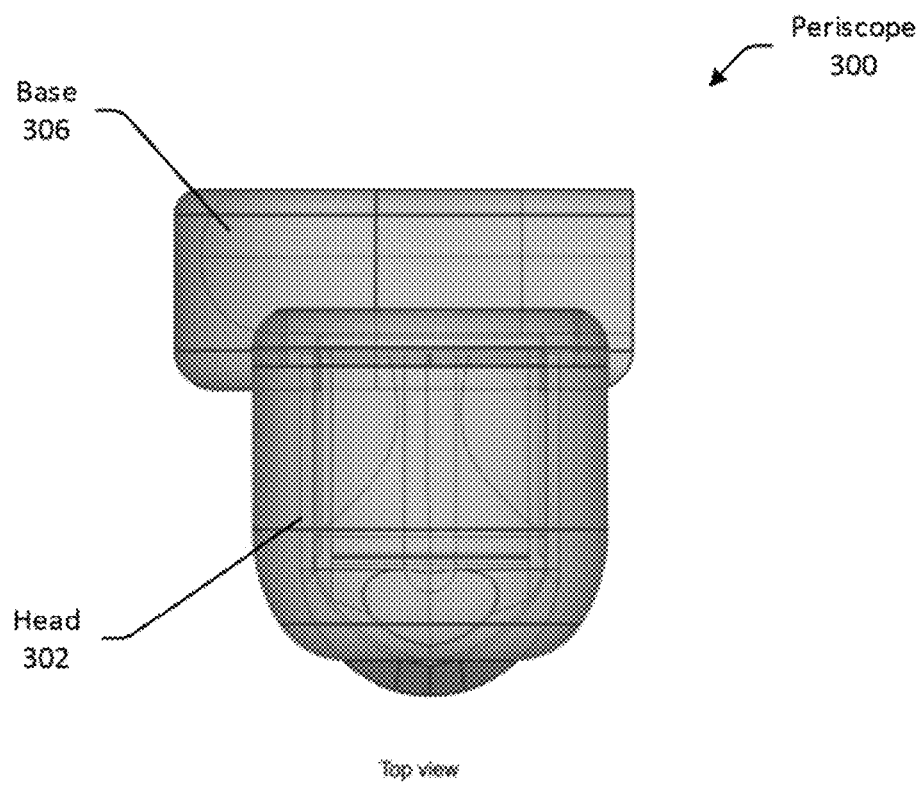
FIG. 3E is a top view of a head of the dental periscope of FIG. 3A.
Figure 3F:
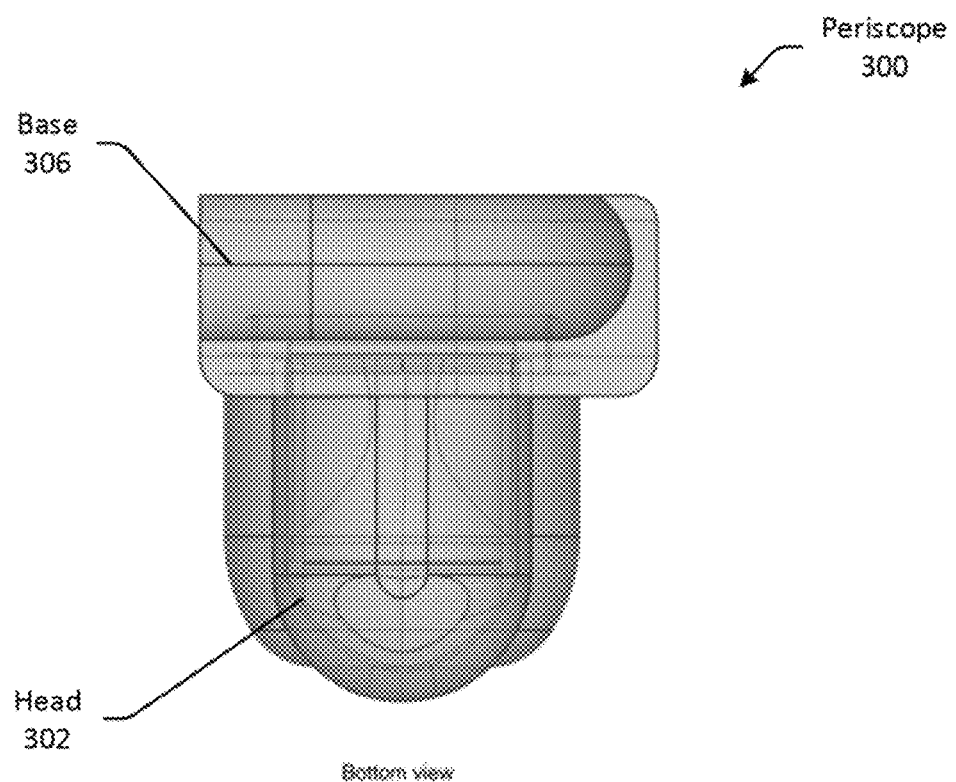
FIG. 3F is a bottom view of the head of the dental periscope of FIG. 3A.

FIG. 3B is a rear view of the periscope 300. FIG. 3C is left side view of the periscope 300. A back surface of the base housing 324 refers to the surface opposite the front surface of the base housing 324, which couples with the mounting clip 312 to mount the periscope 300 to a mobile phone. As shown in the left side view of FIG. 3C as well as the right side view of FIG. 3D, the back surface of the base housing 324 may form an angle with a back surface of a housing of the elongated member 304 that is slightly less than 180 degrees. FIG. 3E is a top view of the head 302. As shown in FIG. 3E, the head 302 and the base 306 are somewhat offset from one another when viewed along a longitudinal axis of the elongated member 304. FIG. 3F is a corresponding bottom view of the head 302.

Figure 3G:
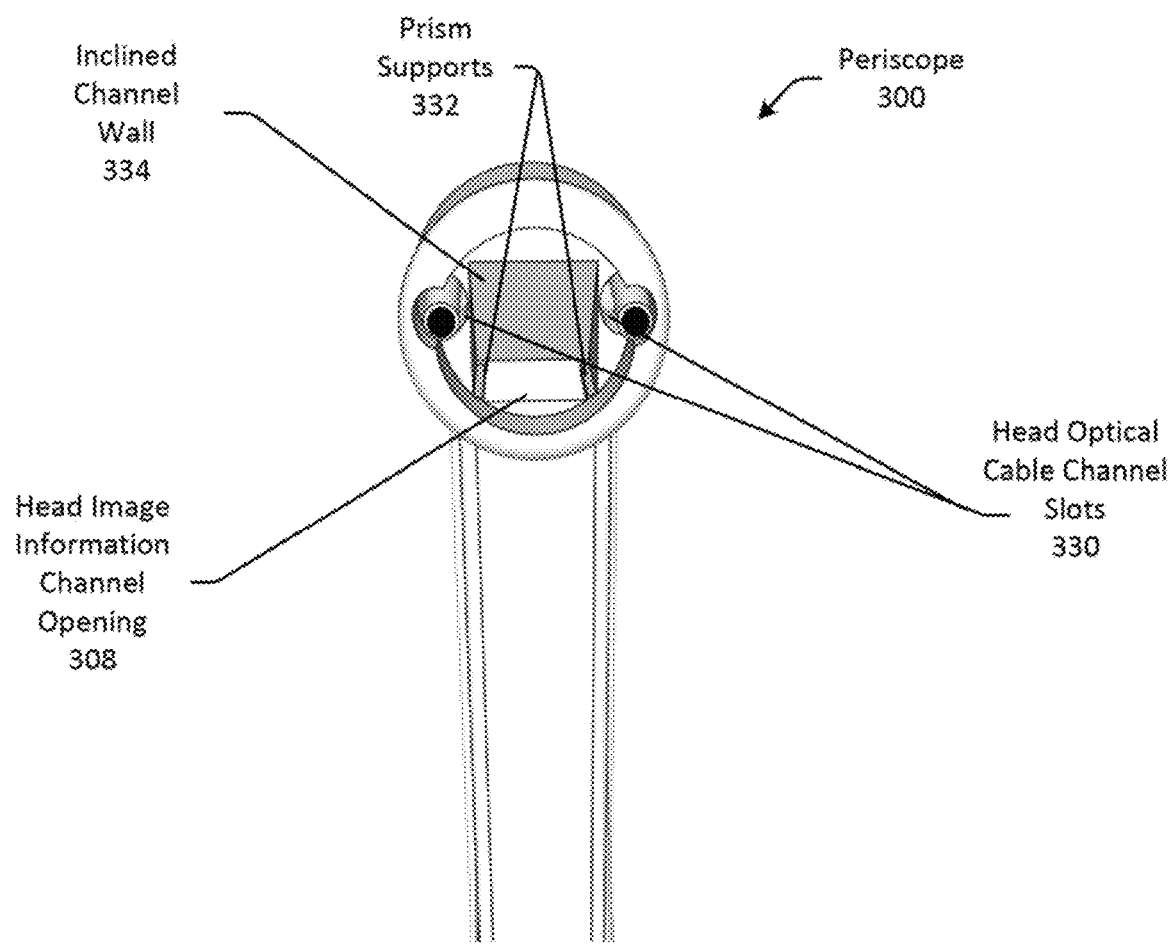
FIG. 3G is a front perspective view of the head of the dental periscope of FIG. 3A.

FIG. 3G is a front perspective view of the periscope 300. As shown in FIG. 3G, the optical cables are received into head optical cable channel slots 300 within the head housing 322. The head optical cable channel slots 300 may be a particular embodiment of the head optical cable channel openings 314. In some embodiments, the elongated member optical cable channel 316 may split upon entering the head 102 into the head optical cable channel slots 330 such that a respective optical cable is received into each slot 330. Also shown in FIG. 3G are prism supports 332 provided in the head image information channel 328. A head prism disposed in the head image information channel 328 may rest on the prism supports 332. Moreover, a diagonal surface of the head prism may contact the inclined channel wall 334 of the head image information channel 328.

Figure 4:
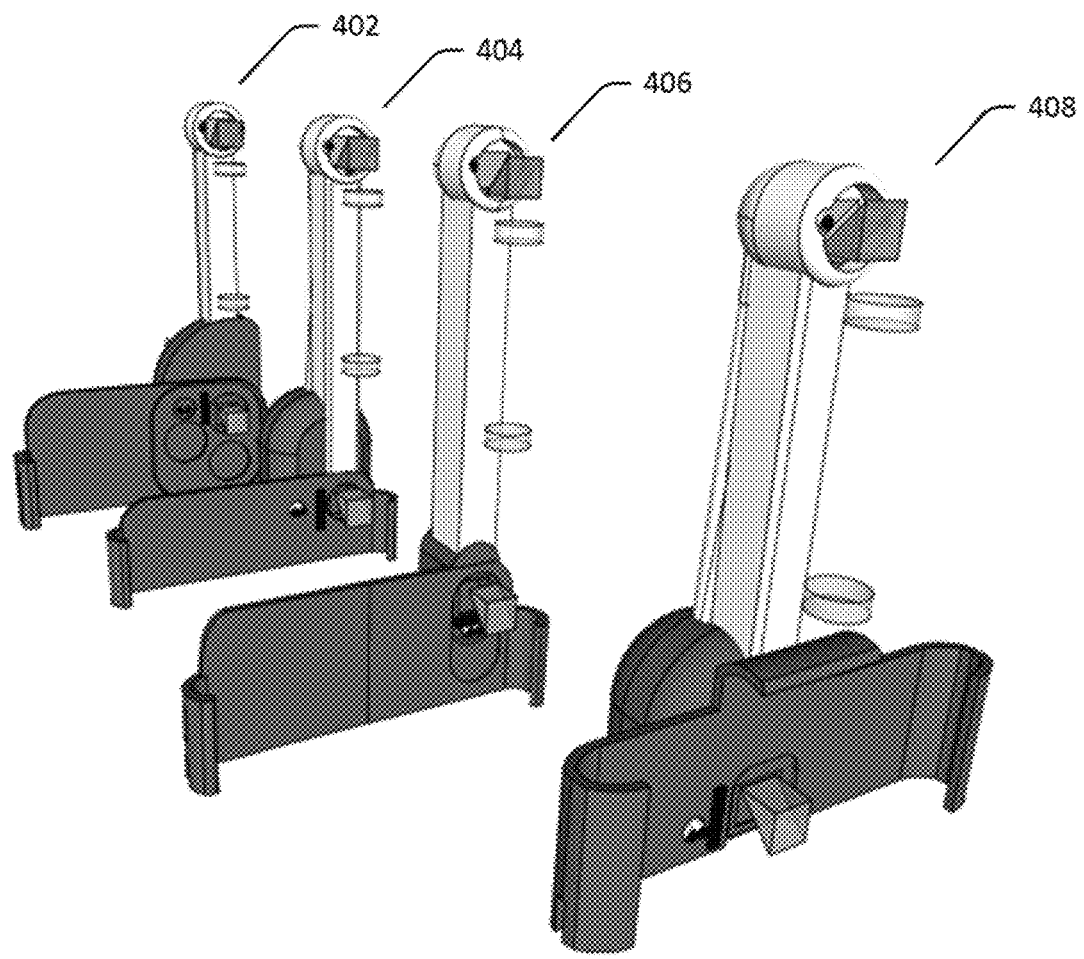
FIG. 4 illustrates left perspective views of dental periscopes with associated mounting clips for different phone models in accordance with some embodiments of the invention.

FIG. 4 illustrates left perspective views of dental periscopes with associated mounting clips for different phone models in accordance with some embodiments of the invention. In embodiment 402, the base image information channel opening of the base/mounting clip of the periscope align with a particular camera of a three-camera configuration such as that found in an iPhone™ 12 Pro. The particular camera is the corner most camera. Further, a light blocking material is provided vertically between the base image information channel opening and the smaller base optical cable channel opening located to the left of the of the base image information channel opening. As described in more detail later in this disclosure, in embodiment 402, recesses may be provided within the mounting clip to accommodate additional cameras on the device that are not flush with a back surface of the device.

In embodiment 404, the mobile device model includes a single camera (e.g., iPhone™ 7/8). In embodiment 404, the base image information channel opening of the base/mounting clip of the periscope is aligned with this single camera. The same is true for embodiment 406 which is an iPhone™ X and embodiment 408 which is a Samsung Galaxy S9. These various embodiments differ with respect to the location of the image sensor and the location of the light source on the mobile phone, and thus, differ with respect to the location of corresponding base image information channel openings and base optical cable channel openings. As a result, the various embodiments also differ with respect to the location of the light blocking element on the mounting clip.

FIGS. 5A-5D depict various views of a mounting clip 502 and base 504 of a dental periscope. The mounting clip 502 may be configured to mount to a first phone model in accordance with some embodiments of the invention. The first phone model may an iPhone™ 12 Pro. The mounting clip 502 includes a recess 506 that receives one of the multiple protruding image sensors of the phone (e.g., cameras that do not sit flush on a back surface of the phone). The recess 506 may be aligned with a base image information channel opening 508 in the base 504. A prism (e.g., base prism 114, base prism 214) is disposed within a base image information channel of the base 504 that opens up to the base image information channel opening. In some embodiments, one of the perpendicular surfaces of the base prism may sit flush with a back surface of the recess 506. The mounting clip 502 further includes one or more additional recesses 512 to receive additional protruding cameras on the mobile device to maintain the clip 502 flush with a back surface of the phone. The mounting clip 502 further includes an base optical cable channel opening 514 for receiving the optical cables. The mounting clip 502 may have a width that is substantially the same as a width of the corresponding mobile device. The mounting clip 502 may include a right clip protrusion 520 and a left clip protrusion 522 configured to attached onto a right and a left side, respectively, of the mobile device. In some embodiments, the right clip protrusion 520 and/or the left clip protrusion 522 may include openings formed therein to accommodate buttons on the mobile device.

As shown in the top view of FIG. 5C, the base 504 includes another base optical cable channel opening 516 and another base image information channel opening 518 formed in a top surface of a base housing of the base 504. The base optical cable channel opening 516 is depicted as having a substantially oval cross-section and the base optical cable channel opening 518 is depicted as having a substantially rectangular (e.g., square) cross-section. It should be appreciated, however, that other cross-sectional shapes are possible. The base optical cable channel opening 516 may be configured to receive the optical cables. The base optical cable channel opening 516 may represent an interface between the elongated member optical cable channel of the elongated member and the base optical cable channel of the base 504. Similarly, the base image information channel opening 518 may represent an interface between the elongated member image information channel and the base image information channel.

In some embodiments, the shape of the base 504 is dictated by where the one or more image sensor(s) are located on the mobile phone. In some embodiments, the base 504 may have a depth of about 1 inch, a width of about 1.25 inches to about 1.5 inches, and a length of about 2.25 inches to about 2.5 inches.

Referring now to FIGS. 6A-6D, various views of a mounting clip 602 and base 604 of a dental periscope are shown, where the mounting clip 602 is configured to couple to a second phone model in accordance with some embodiments of the invention. The second phone model may be an iPhone™ X. In this embodiment, the mounting clip 602 is configured to couple to a mobile phone having a single image sensor. Left and right clip protrusions 610, 612 may be used to couple the mounting clip 602 to the mobile device. The mounting clip 602 includes a recess 606 that receives the protruding image sensor of the mobile device when affixed to the device. A base image information channel opening 608 may be formed in the recess 606. A base prism may be disposed in a base image information channel of the base 604 such that one of the perpendicular surfaces of the prism connected by the diagonal surface is facing the image sensor of the phone at or near the base image information channel opening 608. In some embodiments, the optical cables may be received through a base optical cable channel opening 614.

In some embodiments, the base 604 may include additional openings in a top surface of the base 604 (FIG. 6C) having a similar cross-sectional shape to the openings 516 and 518 of the base 504. The base 604 may be smaller than the base 504. For instance, the base 604 may have a length of about 1 inch, a width of about 0.5 inches, and a depth of about 0.5 inches to about 0.75 inches. The base 604 may have an oblong (e.g., an elongated oval) longitudinal cross-section in a lengthwise direction (e.g., a direction from the base 604 to a head of the periscope).

Referring now to FIGS. 7A-7D, various views of a mounting clip 702 and a base 704 of a dental periscope are shown, where the mounting clip 702 is configured to couple to a third phone model in accordance with some embodiments of the invention. The third phone model may be an iPhone™ 7/8. In this embodiment, the mounting clip 702 is configured to couple to a mobile phone having a single image sensor. Left and right clip protrusions 712, 714 may be used to couple the mounting clip 702 to the mobile device. The mounting clip 702 includes a recess 706 and a base image information channel opening 708 formed within the recess that faces the image sensor of the mobile device when the mounting clip 702 is attached to the device. A prism is disposed in a base image information channel of the base 704 at or near the base image information channel opening 708. In some embodiments, one of the perpendicular surfaces of the prism connected by the diagonal surface is flush with the base image information channel opening 708. In some embodiments, the mounting clip 702/base 704 further includes a base optical cable channel opening 710 for receiving the optical cables.

In some embodiments, the base 704 may include openings in a top surface of the base (FIG. 7C) having a similar cross-sectional shape to the openings 516 and 518 of the base 504. The base 704 may be longer and wider than the base 604. For instance, the base 704 may have a length of about 1.5 inches, a width of about 1 inch, and a depth of about 0.75 inches to about 1 inch. The base 704 may have an oblong (e.g., a compressed oval) longitudinal cross-section in a lengthwise direction.

Referring now to FIGS. 8A-8D, various views of a mounting clip 802 and a base 804 of a dental periscope are shown, where the mounting clip 802 is configured to couple to a fourth phone model in accordance with some embodiments of the invention. The fourth phone model may be a Samsung Galaxy™ S9. In this embodiment, the mounting clip 802 is configured to couple to a mobile phone having a single image sensor. Left, right, and top clip protrusions 812, 814, 816 may be used to couple the mounting clip 802 to the mobile device. A top clip protrusion 816 is provided in this embodiment to support a weight of the base 804 which is coupled (or integrally formed) with the mounting clip 802 towards a center of clip. The mounting clip 802 includes a recess 806 and a base image information channel opening 808 formed in the recess. The base image information channel opening 808 faces the image sensor of the mobile device when the mounting clip 702 is coupled to the mobile device. A base prism may be disposed in a base image information channel of the base 804 having the base image information channel opening 810 at one end. In some embodiments, one of the perpendicular surfaces of the base prism connected by the diagonal surface is facing the image sensor of the phone and is substantially flush with the base image information channel opening 810. In some embodiments, the mounting clip 802/base 804 further includes a base optical cable channel opening 810 for receiving the optical cables.

In some embodiments, the base 804 may include additional openings having a similar cross-sectional shape to the openings 516 and 518 of the base 504, as shown in the top view of FIG. 8C. The base 804 may have a length of about 1.25 inches to about 1.5 inches, a width of about 1.25 inches, and a depth of about 0.75 inches to about 1 inch. The base 804 may have an oblong (e.g., a compressed oval) longitudinal cross-section in a lengthwise direction similar to the base 704.

Figure 9:
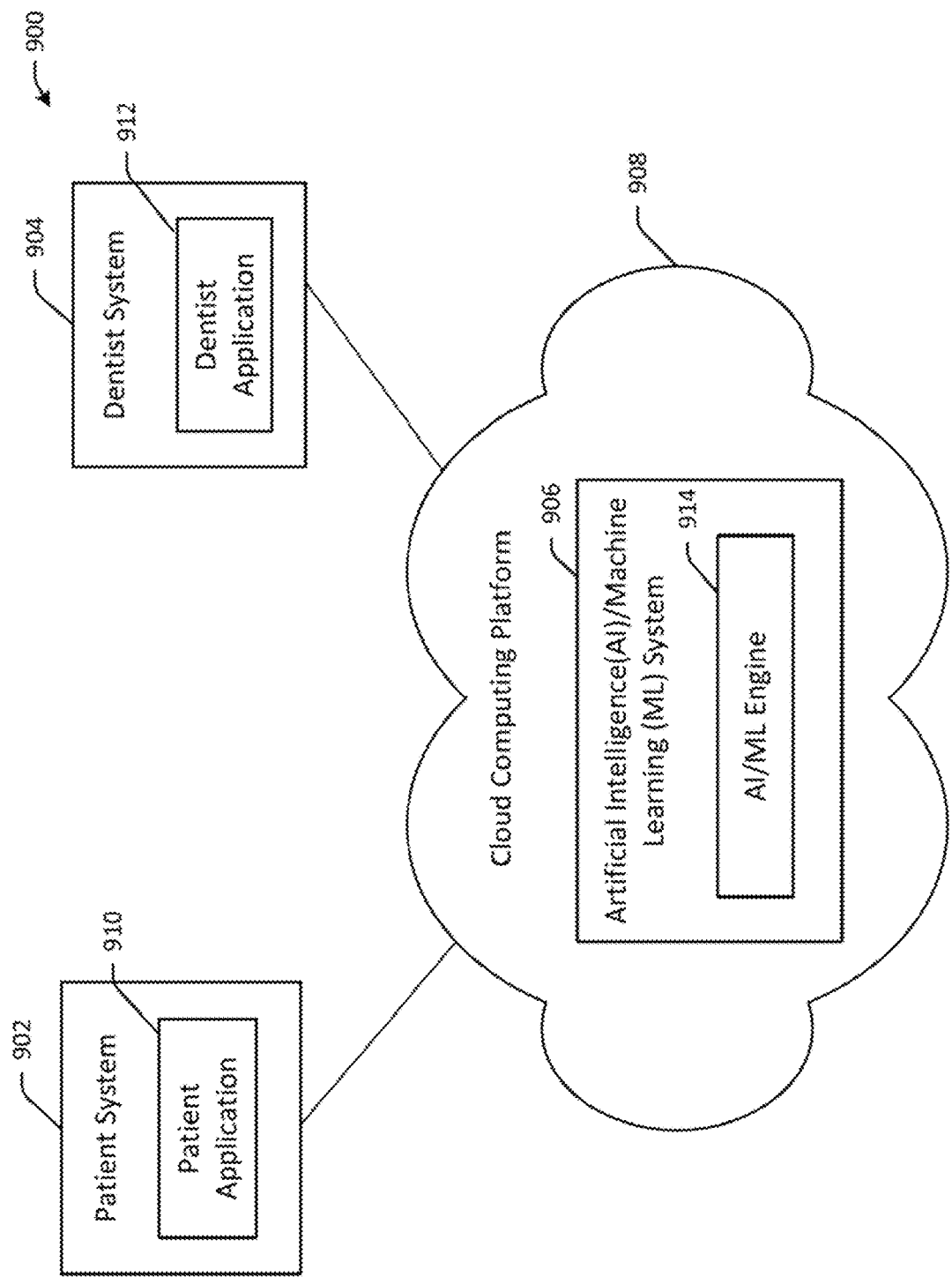
FIG. 9 depicts an illustrative network architecture that supports artificial-intelligence (AI)/machine-learning (ML) for automated remote diagnosis in accordance with some embodiments of the invention.

FIG. 9 depicts an illustrative network architecture 900 associated with artificial intelligence (AI)/machine learning (ML)-based automated remote diagnosis in accordance with some embodiments of the invention. The network architecture 900 includes a patient system 902, a dentist system 904, and an AI/ML, system 906. Each of the patient system 902, the dentist system 904, and the AI/ML, system 906 may include one or more computing devices such as example computing device 1600 depicted in FIG. 16. The AI/ML, system 906 may reside within a cloud computing platform 908. The cloud computing platform 908 one or more servers that provide cloud-based functionality including software-as-a-service (SaaS), cloud storage, and the like. Each of the patient system 902 and the dentist system 904 may be configured to communicate with the cloud computing platform 908 via one or more networks as well as with each other through the cloud computing platform 908. Further, while not depicted in FIG. 9, it should be understood that the patient system 902 may additionally communicate directly (i.e., outside of the cloud computing platform 908) with the dentist system 904 via the one or more networks.

Such networks may include one or more types of communication networks including, without limitation, cable networks, public networks (e.g., the Internet), private networks (e.g., frame-relay networks), wireless networks, cellular networks, telephone networks (e.g., a public switched telephone network), or any other suitable private or public packet-switched or circuit-switched networks. Further, such networks may have any suitable communication range associated therewith and may include, for example, global networks (e.g., the Internet), metropolitan area networks (MANs), wide area networks (WANs), local area networks (LANs), or personal area networks (PANs). In addition, such networks may include communication links and associated networking devices (e.g., link-layer switches, routers, etc.) for transmitting network traffic over any suitable type of medium including, but not limited to, coaxial cable, twisted-pair wire (e.g., twisted-pair copper wire), optical fiber, a hybrid fiber-coaxial (HFC) medium, a microwave medium, a radio frequency communication medium, a satellite communication medium, or any combination thereof.

In some embodiments, the patient system 902 includes a user device, such as a smartphone, tablet, or other mobile device with camera functionality, that is operable by a patient to capture video and/or image data of the patient's mouth including one or more oral structures. A patient application 910 may be running on the patient system 902. For instance, in some embodiments, the patient application 910 may be a mobile application running on a mobile device. Alternatively, the patient application 910 may be a web-based application, a standalone application executable on a desktop or laptop computer, a browser extension or plugin, or the like. The patient application 910 may include computer-executable program code that performs a collection of specific tasks responsive to execution by a processor. In particular, the patient application 910 may include functions, modules, user interfaces, and the like that provide functionality for capturing image/video data of a patient, sending the captured data over a network a remote evaluation and diagnosis, and receiving and presenting diagnosis information indicative of a remote diagnosis made based on the captured patient image/video data, for example.

In particular, in some embodiments, the patient system 902 includes a mobile device having any of the dental periscopes disclosed herein mounted to the device. The device-mounted periscope (e.g., patient system 902) can then be physically maneuvered by the patient to capture video and images of various oral structures. The patient application 910 may send the captured image/video data to a dentist application 912 running on the dentist system 904. In some embodiments, the dentist system 904 may include a user device such as a smartphone, tablet, desktop computer, laptop computer, or the like operable by a dentist or other dental professional.

The dentist may access the patient image/video data via the dentist application 912. The dentist application 912 may include functions, modules, tools, user interfaces, and the like that provide various functionality including providing user interfaces via which a user (e.g., a dentist) can access the patient image/video data; providing tools (e.g., software tools) that enable/facilitate manipulation/editing/labeling of the image/video data or otherwise providing functionality that assists the dentist in visualizing, evaluating, and/or annotating the image/video data; and providing mechanisms for inputting remote diagnosis information indicative of one or more dental diagnoses to the dentist application 912 and sending the remote diagnosis information to the patient system 910 over a network so that it can be presented to the patient via one or more user interfaces of the patient application 910.

Figure 10:
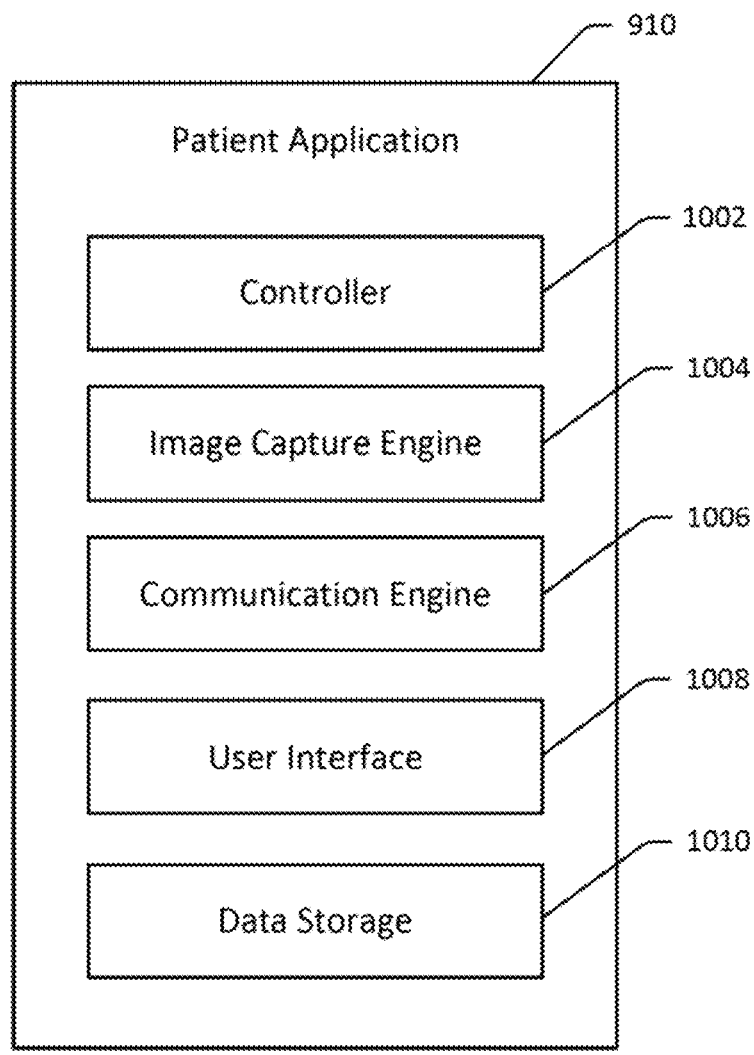
FIG. 10 depicts components of an illustrative patient application in accordance with some embodiments of the invention.
Figure 11:
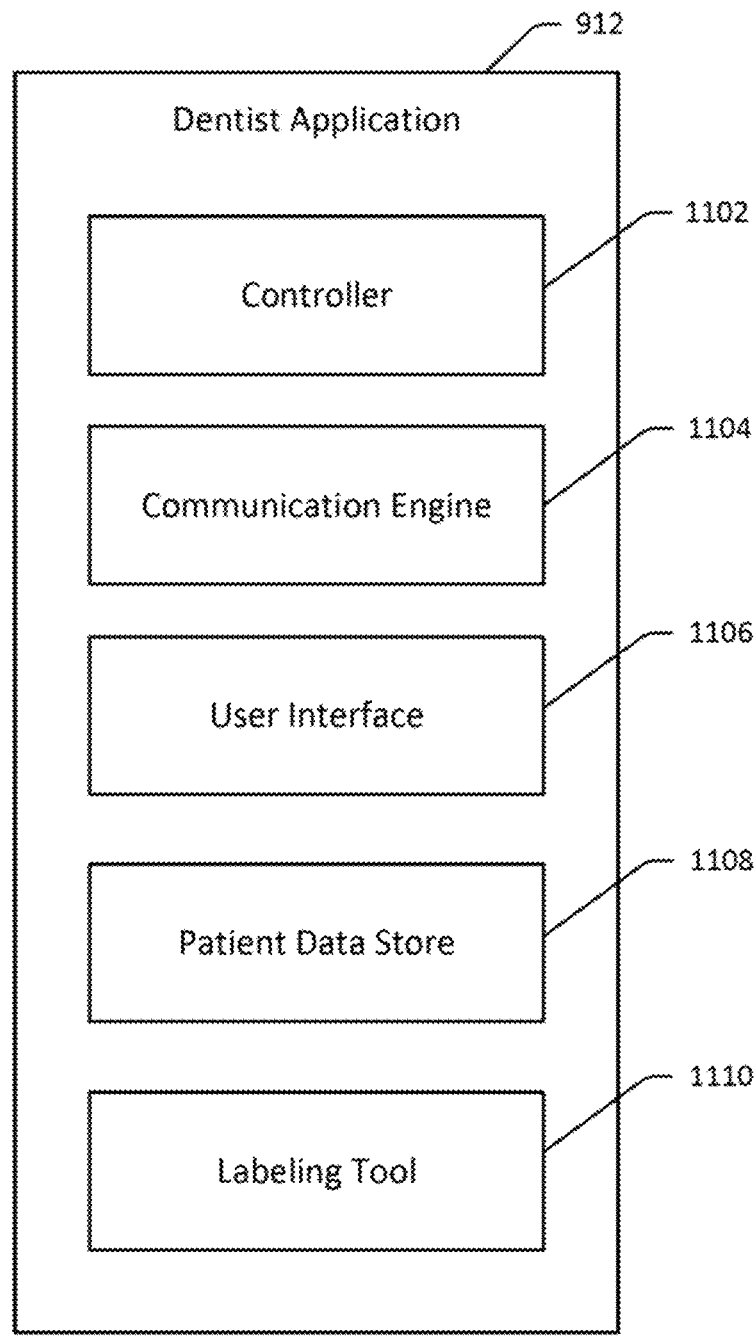
FIG. 11 depicts components of an illustrative dentist application in accordance with some embodiments of the invention.
Figure 13:
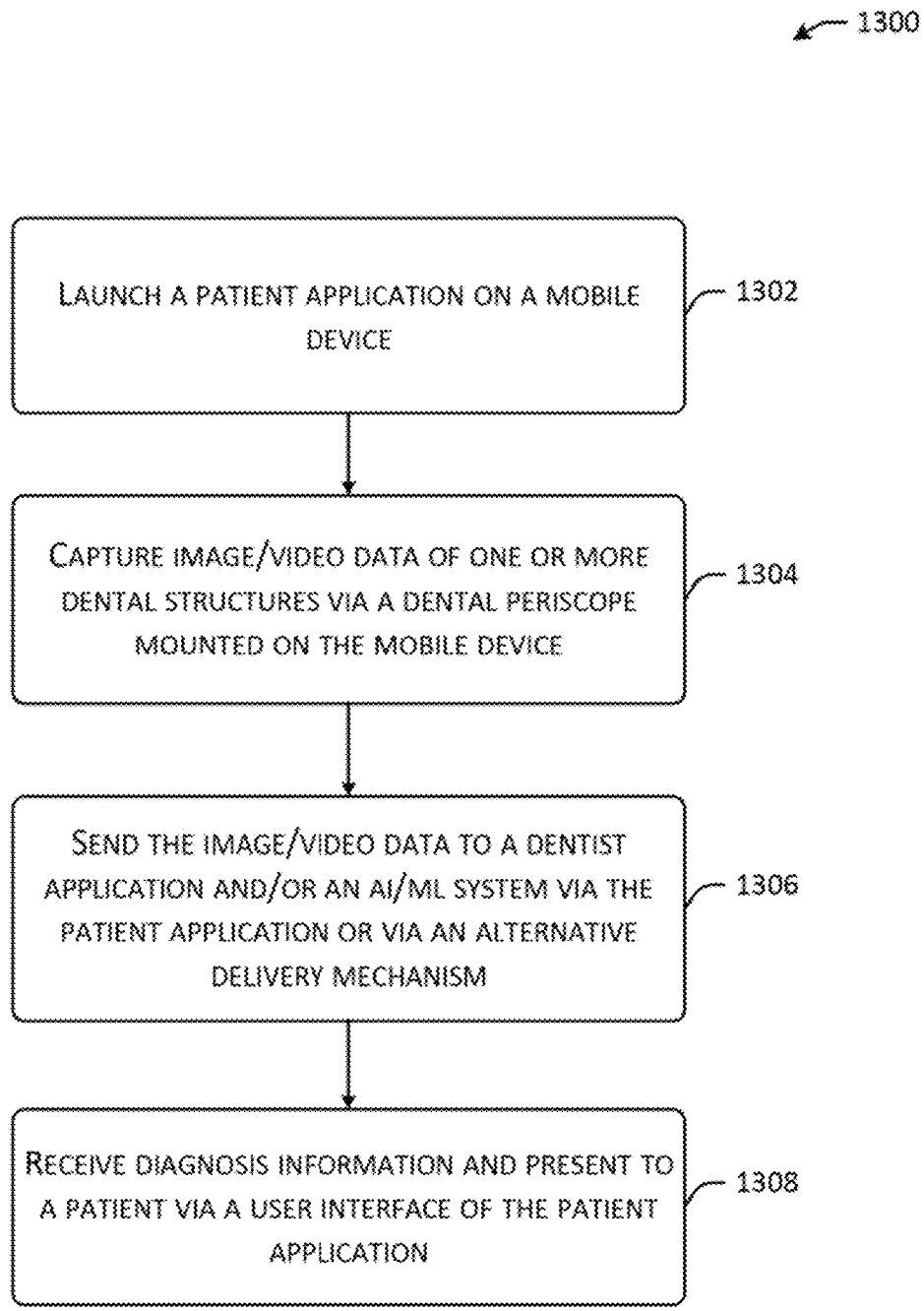
FIG. 13 is a flowchart of an illustrative method for capturing video/image data of a patient using a mobile-device mounted dental periscope, sending the captured data over a network to obtain remote diagnosis information based on the captured data, and presenting the remote diagnosis information via a user interface of a patient application in accordance with some embodiments of the invention.

In some embodiments, the patient application 910 may include the example components depicted in FIG. 10. In particular, referring now FIG. 10, the patient application 910 may include a controller 1002, an image capture engine 1004, a communication engine 1006, a user interface 1008, and data storage 1010. FIG. 11 depicts components of an illustrative dentist application in accordance with some embodiments of the invention. The dentist application 912 may include a controller 1102, a communication engine 1104, a user interface 1106, a patient data store 1108, and a labeling tool 1110. It should be understood that the components depicted in FIGS. 10 and 11 are illustrative and not exhaustive. FIG. 13 is a flowchart of an illustrative method 1300 for capturing image/video data of a patient using a mobile-device mounted dental periscope, sending the captured data over a network to obtain remote diagnosis information based on the captured data, and presenting the remote diagnosis information via a user interface of a patient application in accordance with some embodiments of the invention. FIG. 13 will be described hereinafter with reference to FIGS. 9, 10, and 11. As previously noted, while example embodiments are described herein in the context of dental imaging and dental diagnoses, it should be appreciated that embodiments of the present invention are applicable to any remote medical diagnosis context (i.e., capturing patient image/video data of any anatomical structure and sending the data to a remote location for human and/or automated analysis and evaluation of medical conditions).

Referring now to FIG. 13, at block 1302, a mobile device (e.g., the patient system 902) launches the patient application 910. In some embodiments, the patient system 902 may launch the patient application 910 responsive to user input. For instance, a patient may click an icon on the mobile device to launch the patient application 910. Alternatively, after a dental periscope is mounted on the mobile device, a patient may push a button on the periscope that triggers the mobile device to launch the patient application 910.

At block 1304, the patient may utilize the mobile-device mounted dental periscope to maneuver the device and periscope to capture video and image data of various oral structures. In particular, in some embodiments, after launching the patient application 910, the controller 1002 of the patient application 910 may instruct and control the image capture engine 1004 of the patient application 910 to access the camera functions on the device and capture image/video data within the patient application 910 of various oral structures as the patient maneuvers and manipulates the mobile device-mounted periscope within their mouth. In other embodiments, the patient may access a camera application on their mobile device first, capture the image/video data through the camera application, and then launch the patient application 910 to upload the image/videos to a secure portal or otherwise send the image/videos to the dentist system 904 and/or the AI/ML system 906. The oral structures may include buccal surfaces, occlusal surfaces, and/or medial surfaces of the teeth; outer and/or inner surfaces of the lips; the gingiva; the hard palate; the soft palate; the buccal mucosa; tonsils; the uvula; the floor of the mouth; bottom, top, and/or side surfaces of the tongue; the lingual frenulum; the superior labial frenulum; the inferior labial frenulum; or any other oral structure.

In some embodiments, the patient may be guided in real-time via instructions provided through the patient application 910 to capture images/video of specific dental structures or images/video from specific angles. For example, a dentist or dental assistant may guide the patient through oral instructions received in real-time through the patient application 910 or while connected on a separate phone call. In some embodiments, image information captured by a camera on the mobile device having a dental periscope mounted thereon in accordance with an embodiment of the present invention may be sent, in real-time via the communication engine 1006 of the patient application 910, to the dentist application 912 to enable the dental assistant to provide instructions to the patient in real-time.

Alternatively, the patient may capture the image/video data offline either directly through the patient application 910 accessing the camera functionality of the phone or independently using the camera functionality directly. In some embodiments, the patient may be able to connect the mobile device to another device (e.g., a smart television, a smart device with a display and speaker, etc.) such that the patient can see what is in the camera's FOV as the mobile device-mounted periscope is maneuvered around within the patient's mouth. For instance, the communication engine 1006 may be used to establish a Bluetooth™ connection or the like to the other device with a display.

In some embodiments, irrespective of the mechanism employed to capture the image/video data, at block 1306, the controller 1002 of the patient application 910 may instruct the communication engine 1006 of the patient application 910 to access one or more network interfaces of the mobile device to send the captured patient image/video data to the remotely executing dentist application 912 and/or to the AI/ML system 914 residing in the cloud computing platform 908. In some embodiments, the patient application 910 may send the image/video data to the dentist application 912 through the cloud computing platform 908 and/or through one or more networks independently of the cloud computing platform 908. Functionality of the AI/ML system 914, and in particular, the AI/ML engine 914 will be described in more detail in reference to FIG. 14. Accordingly, the method 1300 of FIG. 13 will be described hereinafter with a focus on the embodiments in which a remote human diagnosis is made based on the captured image/videos.

In some embodiments, the patient image/video data may be encrypted and/or sent through a secure communication link to the dentist application 912 to protect the patient's privacy. In some embodiments, the patient may utilize the patient application 910 to upload the captured data to a secure portal associated with the dentist system 904. In some embodiments, the captured image/video data may also be maintained within data storage 1010. The data storage 1010 may include memory, hard disk storage, or the like residing on the patient system 902 and which is accessible by the patient application 910. Alternatively, the data storage 1010 may refer to databases or other data stores accessible by the patient application 910.

In some embodiments, a dentist or other professional (e.g., dental assistant) may access the patient image/video data received by the dentist system 904 using the dentist application 912, and may review the data to provide a diagnosis of one or more dental conditions. In some embodiments, the received patient image/video data may be stored in a patient data store 1108 maintained by the dentist application 912. The patient data store 1108 may store respective patient data for multiple patients. In some embodiments, the dentist application 912 may locate a profile in the patient data store 1108 that is associated with the patient and store the received image/video data in the patient's profile.

As previously described, the dentist application 912 may include one or more user interfaces 1106 that include various tools/features that enable the dentist to manipulate the image/video data (e.g., zoom in/out, rotate image/videos, enhance clarity of video or images, perform a visual comparison of the data being evaluated to historical patient image/video data, etc.). In some embodiments, the dentist may utilize the dentist application 912 to generate diagnosis information indicative of one or more diagnosed dental conditions. For instance, the dentist may use a dictation function embedded in the dentist application or provided independently on the dentist system 904 to record their findings. Alternatively, or additionally, the dentist may select from various drop-down options or otherwise selectable criteria within the dentist application 912 to indicate findings and generate the diagnosis information indicative of the diagnosed dental conditions. Still further, the dentist may utilize the labeling tool 1110 to edit, modify, or otherwise annotate the image/video data.

Figure 15:
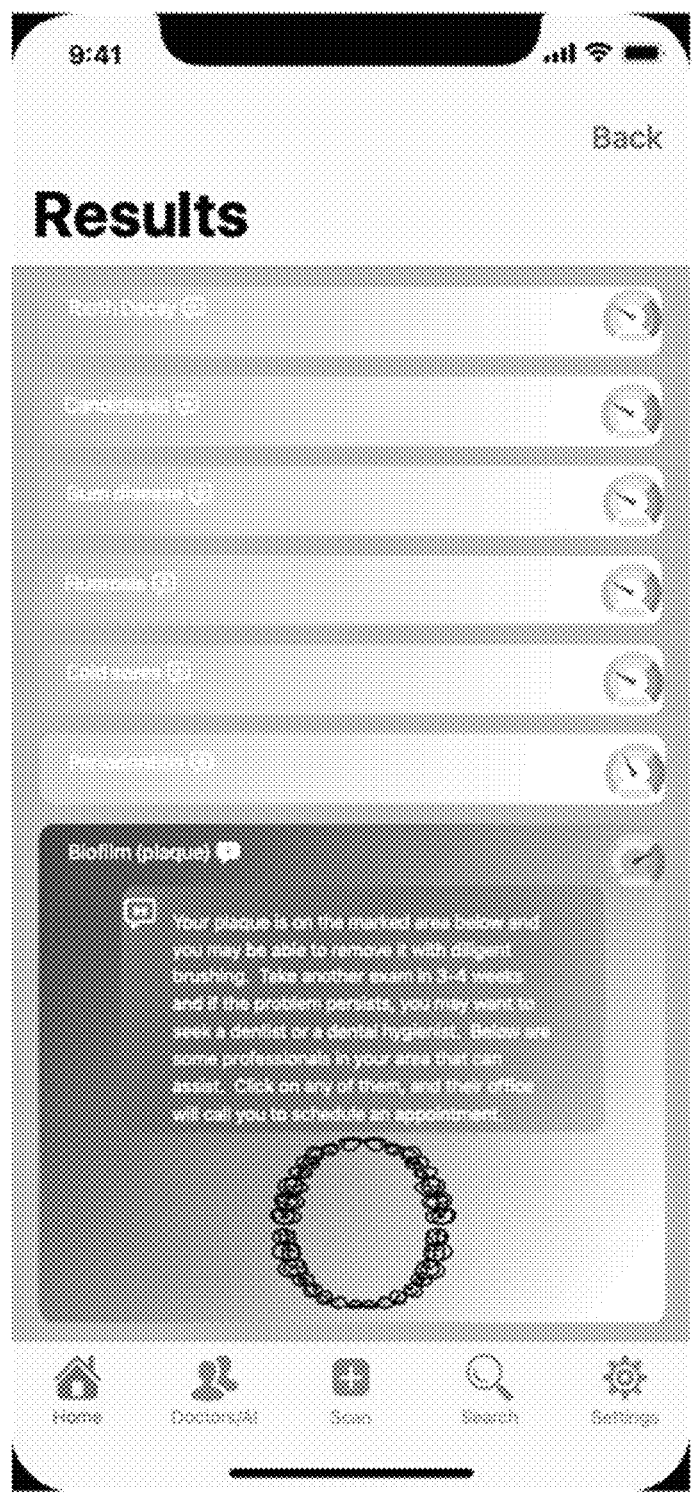
FIG. 15 depicts an example user interface of a patient application via which remote diagnosis information may be presented to a patient in accordance with some embodiments of the invention.

After generating the diagnosis information, the controller 1102 of the dentist application 912 may instruct the communication engine 1104 to send the diagnosis information to the patient application 910. At block 1308, the patient application may receive the diagnosis information and present it to the patient via one or more user interfaces 1008 of the patient application 910. For instance, the diagnosis information may be presented on a display of the patient system 902 within a user interface 1008 of the patient application 910. FIG. 15 depicts an example presentation of diagnosis information 1500. In particular, the diagnosis information 1500 may include various categories of potential dental conditions that any patient may face along with an indication as to whether the patient has been diagnosed with that condition or the patient's risk level for that condition, as revealed by the patient image/video data. In some embodiments, the patient's risk level for various conditions—as determined based on the patient's image/video data—may be indicated using text, graphical elements, or the like.

In some embodiments, the various medical conditions may be expandable to reveal more detailed information. For instance, as depicted in FIG. 15, the biofilm (plaque) category is expanded to reveal a detailed dental diagnosis of the condition for the patient. The detailed diagnostic information may also include an annotated version of the patient's image/video data to draw the patient's attention to specific features in the image/video data, to reveal with more specificity what characteristics of the data motivated the diagnosis, and so forth. Any of a variety of dental conditions may be diagnosed including, without limitation, caries, lesions, gum disease (e.g., gingivitis, periodontitis, etc.), biofilm (e.g., plaque), oral infections, changes to the shape/contour of teeth or other oral structures (e.g., teeth grinding, chipped tooth, crooked teeth, etc.), and so forth.

Figure 14:
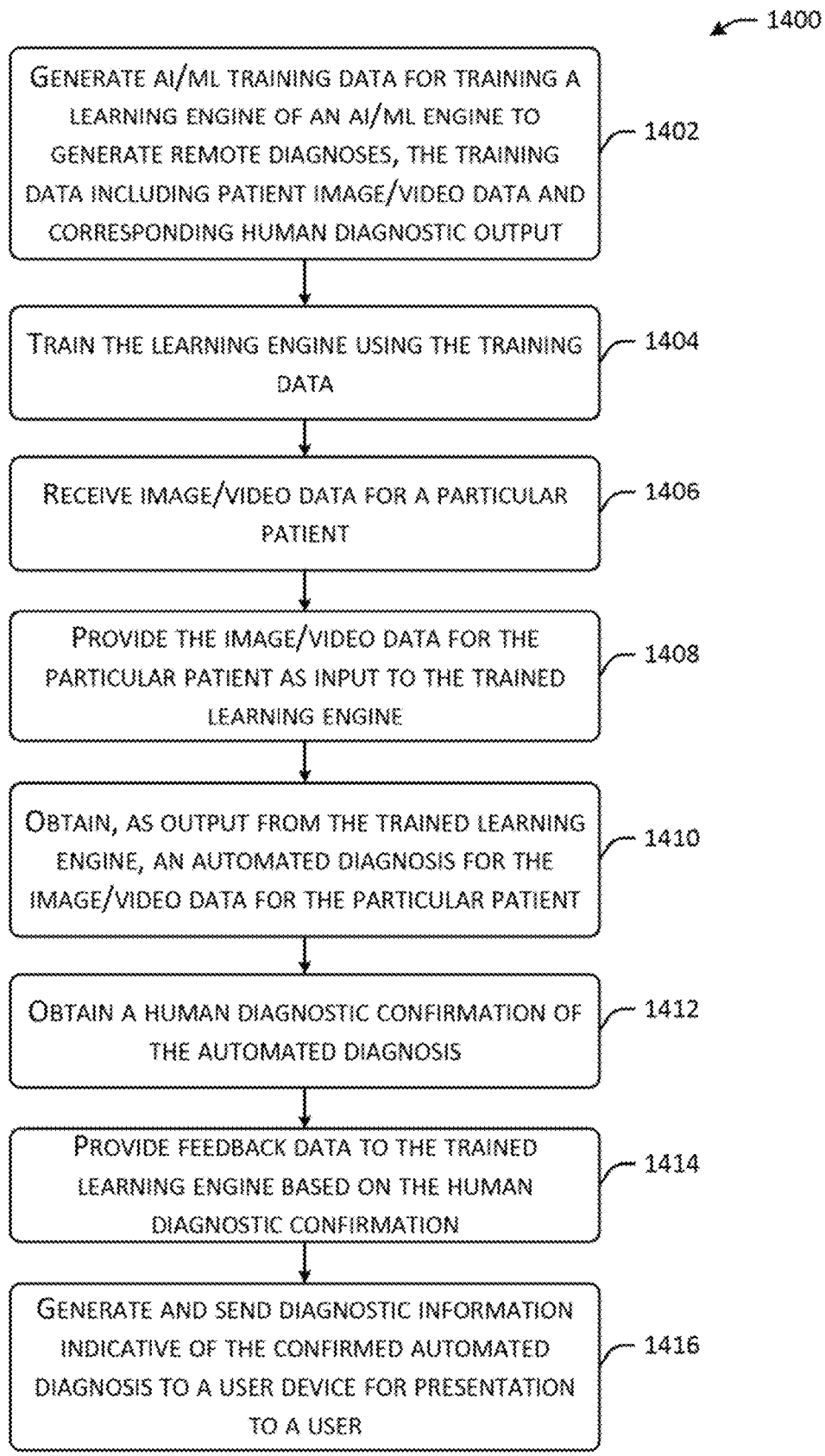
FIG. 14 is a flowchart of an illustrative method for generating and presenting to a patient an automated remote diagnosis generated by a trained AI/ML engine based on video/image data of the patient captured using a mobile-device mounted dental periscope in accordance with some embodiments of the invention.

In some embodiments, the patient image/video data may be provided as input to a trained AI/ML model/algorithm/classifier to generate an automated remote diagnosis. FIG. 14 is a flowchart of an illustrative method 1400 for generating and presenting to a patient an automated remote diagnosis generated by a trained AI/ML engine based on image/video data of the patient captured using a mobile-device mounted dental periscope in accordance with some embodiments of the invention. In some embodiments, the method 1400 may be performed at least in part by an AI/ML engine 914 running on the AI/ML system 906.

Figure 12:
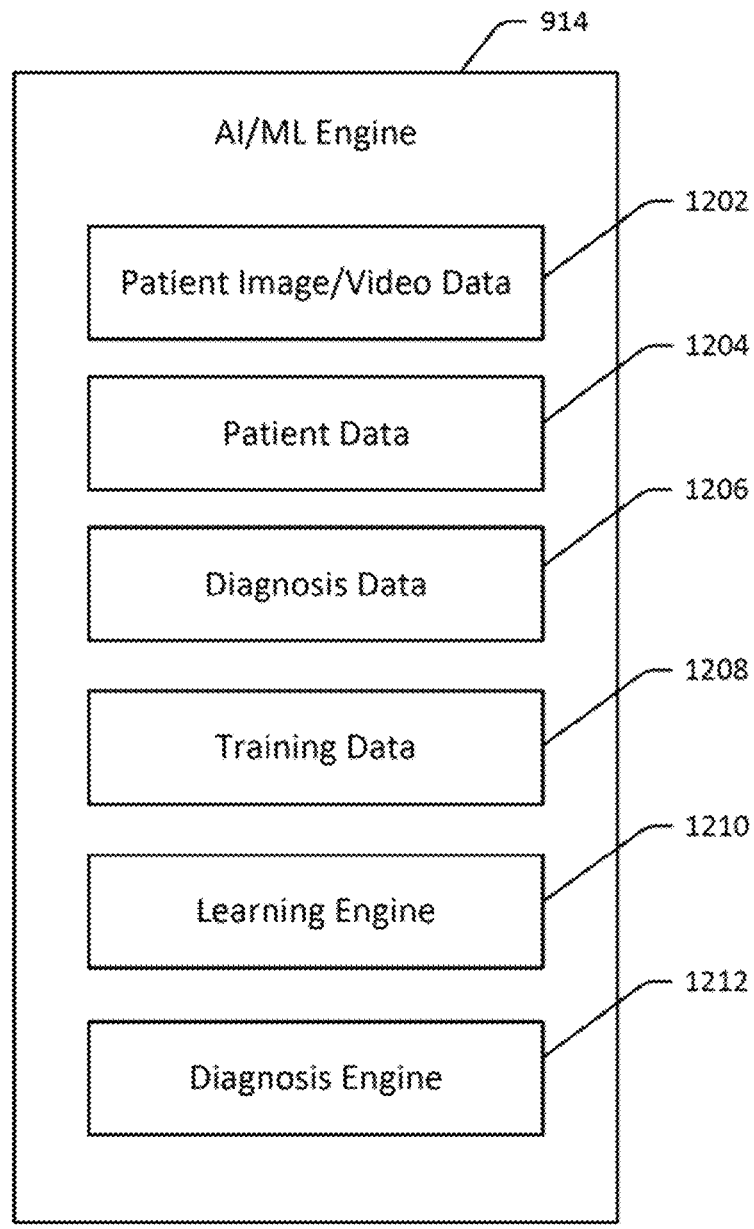
FIG. 12 depicts components of an illustrative AI/ML engine configured to be trained to generate automated remote diagnoses in accordance with some embodiments of the invention.

The AI/ML engine 914 may be configured to train an AI/ML classifier based on historical labeled patient image/video data that serves as ground-truth training data for the classifier. Once trained, new patient image/video data may be fed to the trained classifier as input, and an output of the trained classifier may be provided to the patient as an automated computer vision-based remote diagnosis. FIG. 12 depicts example components of the AI/ML engine 914. The AI/ML engine 914 illustratively includes patient image/video data 1202, patient data 1204, diagnosis data 1206, training data 1208, a learning engine 1210, and a diagnosis engine 1212. The patient image/video data 1202 may include patient image/video data for multiple patients. The patient image/video data 1202 may include, for example, historical image/video data captured over time and relating to multiple patients. The AI/ML engine 914 may receive this historical image/video data from a plurality of patient application 910 instances executing on different patient systems 902. The patient image/video data 1202 may also include patient image/video data recently received from the patient application 910 (or received in real-time), and for which a remote automated diagnosis is requested.

The patient data 1204 may include patient identifying information, patient medical history, or the like for multiple patients. The diagnosis data 1206 may include data indicative of prior diagnoses made, either by a human (e.g., a dentist) or in an automated manner by a trained classifier of the AI/ML engine 914, based on the patient image/video data 1202. The training data 1208 may include, for example, at least a subset of the patient image/video data 1202 that has been annotated/labeled to indicate corresponding confirmed diagnoses made based on the data 1202. The training data 1208 may be provided as ground-truth data to the learning engine 1210. The learning engine 1210 may be an AI/ML model/algorithm/classifier that uses the ground-truth training data 1208 to learn over time to generate automated diagnoses of dental/medical conditions. The learning engine 1210 may employ any suitable form of machine learning including, without limitation, supervised learning, semi-supervised learning, unsupervised learning, or the like. Further, the learning engine 1210 may employ any suitable machine learning algorithm including, without limitation, regression, decision trees, support vector machines (SVMs), Bayesian classification, K-means clustering, deep neural networks (e.g., a convolutional neural network), or the like. The diagnosis engine 1212 may be configured to generate diagnosis information based on an output of the trained learning engine 1210. The diagnosis information may include text, graphics, images (e.g., annotated versions of images captured by the patient using a mobile device-mounted periscope), and the like.

Referring now to FIG. 14, at block 1402, the AI/ML engine 914 may generate the training data 1208 used to train the learning engine 1210 to produce automated diagnoses based on input patient image/video data 1202. In some embodiments, the training data 1208 includes historical input patient image/video data 1202 for which there is a known corresponding human diagnostic output (e.g., a dentist has evaluated the patient image/video data and has provided a diagnosis of one or more dental conditions). In some embodiments, the training data 1208 may be labeled or otherwise annotated to indicate the corresponding human diagnoses.

At block 1404, the learning engine 1210 may be trained based on the training data 1208. In some embodiments, the learning engine 1210 may be iteratively trained based on new ground-truth training data 1208 as it is generated. In some embodiments, the learning engine 1210 may be iteratively trained until a desired level of accuracy (e.g., a desired threshold false positive or false negative rate) is achieved.

At block 1406, the AI/ML engine 914 may receive image/video data for a particular patient. In some embodiments, the patient may use a mobile device-mounted periscope to capture the image/video data offline, which the patient application 910 may then send to the cloud computing platform 908 for use by the AI/ML system 906. Alternatively, the patient application 910 may send the image/video data to the cloud computing platform in real-time as it is captured. At block 1408, the AI/ML engine 914 may provide the image/video data received for the particular patient as input to the trained learning engine 1210. At block 1410, the AI/ML engine 914 may obtain, as output from the trained learning engine 1210, an automated diagnosis of one or more dental conditions (or a diagnosis of the absence of one or more conditions) for the image/video data relating to the particular patient.

In some embodiments, the AI/ML engine 914 may obtain a human confirmation of the automated diagnosis generated by the trained learning engine 1210, at block 1412. This may involve sending the patient image/video data as well as the automated remote diagnosis and associated findings generated by the trained learning engine 1210 to the dentist system 904. A dentist may access this information via the dentist application 912 and provide a human diagnostic output that eithers confirms the accuracy of the automated diagnosis or rejects it. In some embodiments, such as those in which the automated diagnosis is partially correct, the dentist may indicate which aspects of the automated diagnosis are not correct. Then, at block 1414, the human diagnostic confirmation of the automated diagnosis may be provided as feedback data to the trained learning engine 1210 so that the learning engine 1210 can refine its automated diagnosis capabilities.

At block 1416, the diagnosis engine 1210 may generate diagnostic information based on a confirmed automated diagnosis. The diagnostic information may identify the condition(s) diagnosed and/or determined not to be present and may include any of the example types of information depicted in FIG. 15, for example. The AI/ML engine 914 may then send the diagnostic information to the patient application 910 for presentation to the patient via a user interface 1008 of the patient application 910. The diagnostic information may also be stored as part of the diagnosis data 1206, and may be used as ground-truth training data in the future. In some embodiments, the diagnosis engine 1210 may generate the diagnostic information based on the automated diagnosis outputted by the trained learning engine 1210 without first obtaining a human diagnostic confirmation if, for example, a threshold confidence is achieved with respect to the accuracy of the trained learning engine 1210. However, in such embodiments, a human diagnostic confirmation may nonetheless be sought after the diagnostic information is generated and/or presented to the patient. If the human diagnostic output determines that modifications are needed to the diagnosis or to the diagnostic information generally, modified diagnostic information may be generated and sent to the patient application 910.

Figure 16:
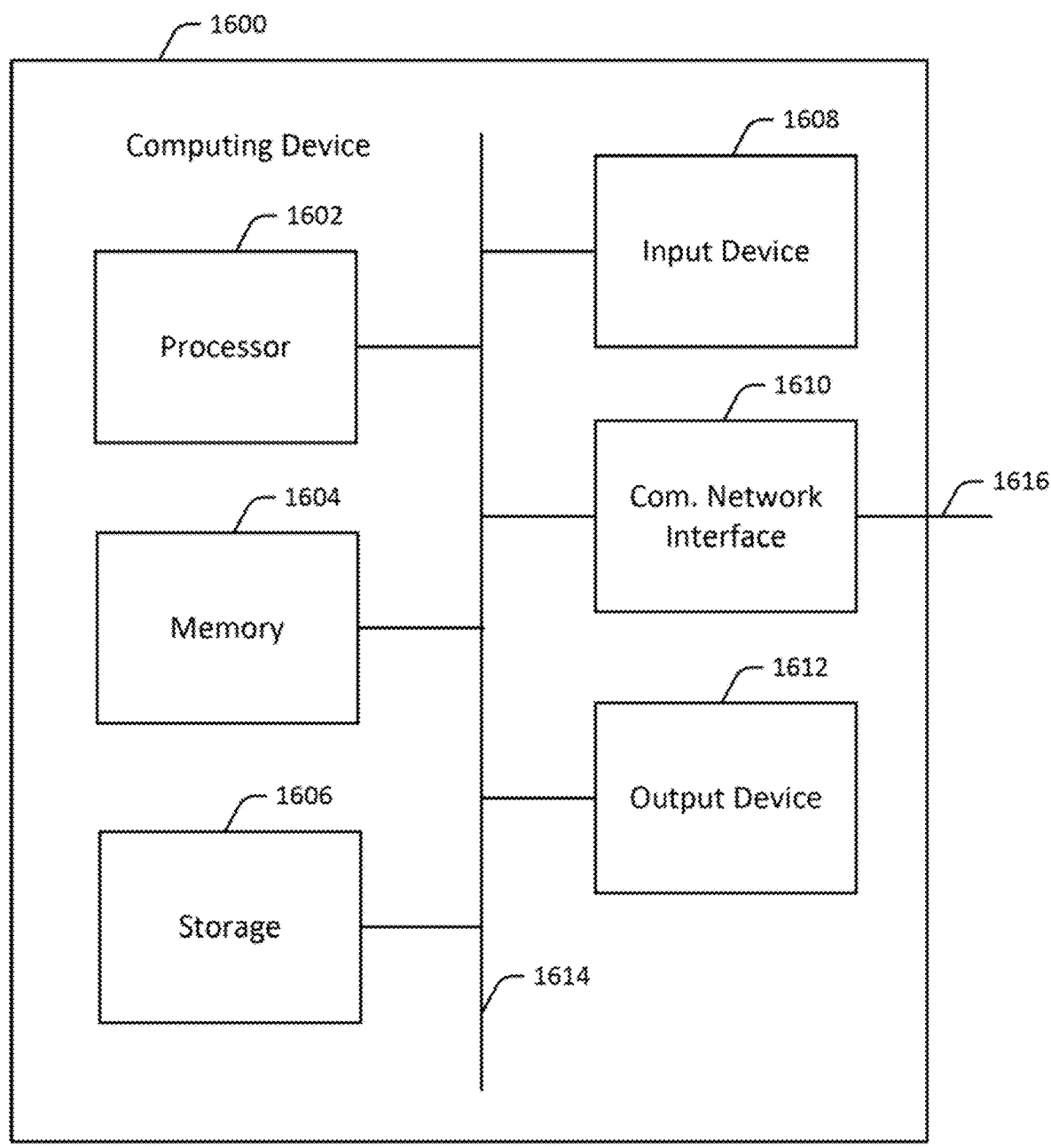
FIG. 16 depicts an example computing device that can be used to implement functionality of one or more systems of the network architecture of FIG. 9.

FIG. 16 depicts an example computing device that can be used to implement functionality of one or more systems of the network architecture of FIG. 9. FIG. 16 depicts an example computing device 1600. Any of the systems, engines, datastores, and/or networks described herein may comprise one or more instances of the computing device 1600. In some example embodiments, functionality of the computing device 1600 is improved to the perform some or all of the functionality described herein. The computing device 1600 comprises a processor 1602, memory 1604, storage 1606, an input device 1608, a communication network interface 1610, and an output device 1612 communicatively coupled to a communication channel 1614. The processor 1602 is configured to execute executable instructions (e.g., programs). In some example embodiments, the processor 1602 comprises circuitry or any processor capable of processing the executable instructions.

The memory 1604 stores data. Some examples of memory 1604 include storage devices, such as RAM, ROM, RAM cache, virtual memory, etc. In various embodiments, working data is stored within the memory 1604. The data within the memory 1604 may be cleared or ultimately transferred to the storage 1606.

The storage 1606 includes any storage configured to retrieve and store data. Some examples of the storage 1606 include flash drives, hard drives, optical drives, cloud storage, and/or magnetic tape. Each of the memory system 1604 and the storage system 1606 comprises a computer-readable medium, which stores instructions or programs executable by processor 1602.

The input device 1608 is any device that inputs data (e.g., mouse and keyboard). The output device 1612 outputs data (e.g., a speaker or display). It will be appreciated that the storage 1606, input device 1608, and output device 1612 may be optional. For example, the routers/switchers may comprise the processor 1602 and memory 1604 as well as a device to receive and output data (e.g., the communication network interface 1610 and/or the output device 1612).

The communication network interface 1610 may be coupled to a network (e.g., network 908) via the link 1616. The communication network interface 1610 may support communication over an Ethernet connection, a serial connection, a parallel connection, and/or an ATA connection. The communication network interface 1610 may also support wireless communication (e.g., 802.11 technologies, WiMax, LTE, 5G, etc.). It will be apparent that the communication network interface 1610 may support many wired and wireless standards.

It will be appreciated that the hardware elements of the computing device 1600 are not limited to those depicted in FIG. 16. A computing device 1600 may comprise more or less hardware, software and/or firmware components than those depicted (e.g., drivers, operating systems, touch screens, biometric analyzers, and/or the like). Further, hardware elements may share functionality and still be within various embodiments described herein. In one example, encoding and/or decoding may be performed by the processor 1602 and/or a co-processor located on a GPU (i.e., NVidia).

It will be appreciated that an "engine," "system," "datastore," and/or "database" may comprise software, hardware, firmware, and/or circuitry. In one example, one or more software programs comprising instructions capable of being executable by a processor may perform one or more of the functions of the engines, datastores, databases, or systems described herein. In another example, circuitry may perform the same or similar functions. Alternative embodiments may comprise more, less, or functionally equivalent engines, systems, datastores, or databases, and still be within the scope of present embodiments. For example, the functionality of the various systems, engines, datastores, and/or databases may be combined or divided differently. The datastore or database may include cloud storage. It will further be appreciated that the term "or," as used herein, may be construed in either an inclusive or exclusive sense. Moreover, plural instances may be provided for resources, operations, or structures described herein as a single instance.

The datastores described herein may be any suitable structure (e.g., an active database, a relational database, a self-referential database, a table, a matrix, an array, a flat file, a documented-oriented storage system, a non-relational No-SQL system, and the like), and may be cloud-based or otherwise.

The systems, methods, engines, datastores, and/or databases described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an API).

The performance of certain of the operations may be distributed among the processors, not only residing within a single machine, but deployed across a number of machines. In some example embodiments, the processors or processor-implemented engines may be located in a single geographic location (e.g., within a home environment, an office environment, or a server farm). In other example embodiments, the processors or processor-implemented engines may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

The present invention(s) are described above with reference to example embodiments. It will be apparent to those skilled in the art that various modifications may be made and other embodiments may be used without departing from the broader scope of the present invention(s). Therefore, these and other variations upon the example embodiments are intended to be covered by the present invention(s).

The invention claimed is:

1. A mobile device-mountable periscope for dental imaging, comprising:
  a head including a head image information channel, the head image information channel having a head image information channel opening, the head being configured to receive image information via the head image information channel opening;
  a base including a base image information channel, the base image information channel having a base image information channel opening, the base being configured to provide the image information to an image sensor of a mobile device via the base image information channel opening;
  an elongated member including an elongated member image information channel, the elongated member image information channel having a first elongated member image information channel opening coupled to the head image information channel, the elongated member image information channel having a second elongated member image information channel opening coupled to the base image information channel, the elongated member being configured to pass the image information from the head to the base via the elongated member image information channel;
  a head prism disposed within the head image information channel, the head prism being configured to redirect the image information from the head image information channel to the elongated member image information channel towards the base;
  a base prism disposed within the base information channel, the base prism being configured to redirect the image information from the elongated member image information channel towards the image sensor of the mobile device;
one or more optical cable channels within the base, the elongated member and the head, the one or more optical cable channels being separate from the head image information channel, from the elongated member image information channel, and from the base image information channel; and
one or more optical cables disposed within the one or more optical cable channels, the one or more optical cables configured to carry light from a light source of the mobile device to one or more head optical channel opening.

2. The mobile device-mountable periscope of claim 1, further comprising a mounting clip configured to mount the mobile device-mountable periscope on the mobile device.

3. The mobile device-mountable periscope of claim 2, wherein the base image information channel opening faces at least one camera of the mobile device when the mounting clip is attached to the mobile device.

4. The mobile device-mountable periscope of claim 2, wherein the mounting clip comprises a recess, and wherein the base image information channel opening is formed in the recess.

5. The mobile device-mountable periscope of claim 2, wherein the mounting clip is integrally formed with the base.

6. The mobile device-mountable periscope of claim 2, wherein the mounting clip includes a left side portion configured to clip to a left side of the mobile phone and a right side portion configured to clip to a right side of the mobile phone.

7. The mobile device-mountable periscope of claim 2, wherein the mounting clip is detachably coupled to the dental periscope.

8. The mobile device-mountable periscope of claim 2, wherein the mounting clip is integrally formed with at least one of the head, the elongated member or the base.

9. The mobile device-mountable periscope of claim 1, wherein the head further includes one or more head optical cable channels, the base further includes one or more base optical cable channels, and the elongated member further includes one or more elongated member optical cable channels, the one or more optical cable channels including the one or more head optical cable channels, the one or more base optical cable channels, and the one or more elongated member optical cable channels.

10. The mobile device-mountable periscope of claim 9, wherein the one or more base optical cable channels comprises one or more base optical cable channel openings for receiving the one or more optical cables.

11. The mobile device-mountable periscope of claim 10, wherein the mounting clip comprises a light blocking element disposed between the base image information channel opening and the one or more base optical channel openings.

12. The mobile device-mountable periscope of claim 1, wherein the head image information channel comprises a pair of prism supports that support the head prism within the head image information channel.

13. The mobile device-mountable periscope of claim 1, wherein the base is detachably coupled to the elongated member.

* * * * *